US008425914B2

(12) United States Patent
Haffer et al.

(10) Patent No.: US 8,425,914 B2
(45) Date of Patent: Apr. 23, 2013

(54) METHODS FOR ENHANCED SOMATOSTATIN IMMUNOGENICITY IN THE TREATMENT OF OBESITY

(75) Inventors: Keith N. Haffer, Garretson, SD (US); James Larrick, Sunnyvale, CA (US); Andrew R. Mendelsohn, Sunnyvale, CA (US)

(73) Assignee: Braasch Biotech LLC, Garretson, SD (US)

( * ) Notice: Subject to any disclaimer, the term of this patent is extended or adjusted under 35 U.S.C. 154(b) by 0 days.

(21) Appl. No.: 12/523,952

(22) PCT Filed: Jun. 24, 2009

(86) PCT No.: PCT/US2009/048429
§ 371 (c)(1),
(2), (4) Date: Jan. 5, 2010

(87) PCT Pub. No.: WO2009/158395
PCT Pub. Date: Dec. 30, 2009

(65) Prior Publication Data
US 2011/0195080 A1    Aug. 11, 2011

Related U.S. Application Data

(60) Provisional application No. 61/075,656, filed on Jun. 25, 2008.

(51) Int. Cl.
*C07K 14/655* (2006.01)
*C12N 9/1033* (2006.01)
*A61K 2039/55566* (2006.01)
*C07K 2319/00* (2006.01)
*C07K 2319/31* (2006.01)

(52) U.S. Cl.
USPC .................. 424/185.1; 424/198.1; 424/278.1; 514/909

(58) Field of Classification Search .................. None
See application file for complete search history.

(56) References Cited

U.S. PATENT DOCUMENTS

| | | | |
|---|---|---|---|
| 4,446,235 A | 5/1984 | Seeburg | |
| 4,601,980 A | 7/1986 | Goeddel et al. | |
| 6,025,368 A | 2/2000 | Mascarenhas et al. | |
| 6,316,004 B1 | 11/2001 | Lunin et al. | |
| 7,722,881 B2 | 5/2010 | Mendelsohn et al. | |
| 7,943,143 B2 | 5/2011 | Mendelsohn et al. | |
| 2007/0048860 A1 | 3/2007 | Schlom et al. | |
| 2007/0249532 A9 | 10/2007 | Guyon et al. | |
| 2008/0081068 A1 | 4/2008 | Oberegger et al. | |
| 2009/0324629 A1 | 12/2009 | Mendelsohn et al. | |
| 2010/0136037 A1 | 6/2010 | Mendelsohn et al. | |

FOREIGN PATENT DOCUMENTS

| | | |
|---|---|---|
| EP | 0645454 | 1/1997 |
| EP | 1243256 A1 | 9/2002 |
| KR | 1990-7000505 | 8/1990 |
| WO | WO 89/04326 | 5/1989 |
| WO | WO 2005/066344 | 7/2005 |
| WO | WO 2009/157926 | 12/2009 |
| WO | WO 2009/158395 | 12/2009 |

OTHER PUBLICATIONS

Lustig et al, (International Journal of Obesity, 2006, vol. 30, pp. 331-341).*
Shalet et al, Endocrine Reviews, 1998, vol. 19, No. 2, pp. 203-223.*
Bravermean et al. Journal of Medical Case Reports 2010, vol. 4, No. 305, pp. 1-5.*
Laarveld et al, Canadian Journal of Animal Science, 1986, vol. 66, pp. 77-83.*
Notice of Allowance Jan. 28, 2010 with respect to U.S. Appl. No. 12/198,579.
Araki et al. (2008) "Effects of Pravastatin on Obesity, Diabetes, and Adiponectin in Diet-induced Obese Mice" Obesity 16:2068-2073.
Samson et al. (2008) "Gene Therapy for Diabetes: Metabolic Effects of Helper-dependent Adenoviral Exendin 4 Expression in a Diet-induced Obesity Mouse Model" Mol. Ther. 16(11):1805-1812.
Chothia and Lesk (1986) "The Relation Between the Divergence of Sequence and Structure in Proteins" The EMBO Journal, 5(4):823-826.
Danoff et al. (1993) "Intracellular Degradation of Prohormone-Chloramphenicol-Acetyl-Transferase Chimeras in a Pre-Lysosomal Compartment" Eur. J. Biochem., 218(3):1063-1070.
Drackley (2004) "Physiological Adaptations in Transition Dairy Cows" Proc. Minnesota Dairy Herd Health Conf., St. Paul, M.N. University of Minnesota, St. Paul. pp. 74-87.
Drozdowski et al. (2006) "Intestinal Mucosal Adaptation" World of Gastroenterol., 12(29):4614-4627.
Fortier et al. (2002) "Insulin-Like Growth Factor-I Enhances Cell-Based Repair of Articular Cartilage" Journal of Bone and Joint Surgery, 84-B(2):276-288.
Greenspan and Di Cera (1999) "Defining Epitopes: It's Not As Easy As It Seems" Nature Biotechnology, 17:936-937.
Jaffe et al. (1996) "Endogenous Growth Hormone (GH)-Releasing Hormone is Required for GH Responses to Pharmacological Stimuli" J. Clin. Investigation, 97(4):934-940.
Lewendon and Shaw (1993) "The $pK_a$ of the Catalytic Histidine Residue of Chloramphenicol Acetyltransferase" Biochem. J., 290:15-19.
Lewendon et al. (1994) "Replacement of Catalytic Histidine-195 of Chloramphenicol Acetyl Transferase: Evidence for a General Base Role for Glutamate" Biochemistry, 33(7):1944-1950.

(Continued)

*Primary Examiner* — Bridget E Bunner
*Assistant Examiner* — Fozia Hamud
(74) *Attorney, Agent, or Firm* — Merchant & Gould, P.C.

(57) ABSTRACT

Compositions and methods are provided for treatment growth hormone and/or insulin-like growth factor 1 deficiency in a patient in need of such treatment. Compositions and methods include novel vaccines that provide immunogenicity for somatostatin and result in the increased release of endogenously produced growth hormone and/or insulin-like growth factor 1.

2 Claims, 6 Drawing Sheets

OTHER PUBLICATIONS

Liang et al. (2008) "Construction and Evaluation of the Eukaryotic Expression Plasmid Encoding Two Copies of Somatostatin Genes Fused with Hepatitis B Surface Antigen Gene S" Vaccine, 26(23):2935-2941.

Lin et al. (1998) "Evolution of Neuroendocrine Peptide Systems: Gonadotropin-Releasing Hormone and Somatostain" Comp. Biochem. Physiol. C., 119(3):375-388.

Liu and LeRoith (1999) "Insulin-Like Growth Factor I is Essential for Postnatal Growth in Response to Growth Hormone" Endocrinology, 140(11):5178-5184.

Mikayama et al. (1993) "Molecular Cloning and Functional Expression of a cDNA Encoding Glycosylation-Inhibiting Factor" Proc. Natl. Acad. Sci. USA, 90:10056-10060.

Muderhwa et al. (1999) "Oil-in-Water Liposomal Emulsions: Characterization and Potential use in Vaccine Delivery" J. Pharm. Sci., 88(12):1332-1339.

Office Action Nov. 16, 2009 with respect to U.S. Appl. No. 12/198,579.

Patel and Srikant (1999) "Somatostatin and it's Receptors" Adv. Mol. Cell. Endocrinol., 3:43-73.

Reichlin S., ed (1987) "Somatostatin: Basic and Clinical Status" Plenum Press, New York and London (pp. 3-50, 146-156, 169-182, 221-228, 267-274).

Rudinger (1976) "Characteristics of the Amino Acids as Components of a Peptide Hormone Sequence" Peptide Hormones. Biol. Council., pp. 5-7.

Spencer (1985) "Hormonal Systems Regulating Growth. A Review" Livestock Production Science, 12:31-46.

Tropea et al. (2009) "Partial Reversal of Rett Syndrome-Like Symptoms in MeCP2 Mutant Mice" PNAS 106(6):2029-2034.

Vickers et al. (2002) "Adult Growth Hormone Treatment Reduces Hypertension and Obesity Induced by an Adverse Prenatal Environment" Journal of Endocrinology, 175:615-623.

White et al. (2000) "Characterization of Chloramphenicol and Florfenicol Resistance in *Escherichia coli* Associated with Bovine Diarrhea" J. of Clinical Microbiology, 38(12):4593-4598.

Extended European Search Report, Oct. 9, 2012, EP Appl. No. 09770928.1.

Robben et al. (1995) "Insertional Re-Activation of a Chloramphenicol Acetyltransferase Misfolding Mutant Protein", Protein Eng. 8(2):159-165.

Scheuren et al. (1998) "Misfolding of Chloramphenicol Acetyltransferase Due to Carboxy-Terminal Truncation can be Corrected by Second-Site Mutations", Protein Engineering 11(12):1211-1217.

* cited by examiner

SEQUENCE LISTING

<160> NUMBER OF SEQ ID NOS: 15

<210> SEQ ID NO 1
<211> LENGTH: 14
<212> TYPE: PRT
<213> ORGANISM: Artificial
<220> FEATURE:
<223> OTHER INFORMATION: Synthetic

<400> SEQUENCE: 1

Ala Gly Cys Lys Asn Phe Phe Trp Lys Thr Phe Thr Ser Cys
1               5                   10

<210> SEQ ID NO 2
<211> LENGTH: 630
<212> TYPE: DNA
<213> ORGANISM: Artificial
<220> FEATURE:
<223> OTHER INFORMATION: Synthetic

<400> SEQUENCE: 2
atggagaaaa aaatcactgg atataccacc gttgatatat cccaatggca tcgtaaagaa       60
cattttgagg catttcagtc agttgctcaa tgtacctata accagaccgt tcagctggat      120
attacggcct ttttaaagac cgtaaagaaa aataagcaca agttttatcc ggcctttatt      180
cacattcttg cccgcctgat gaatgctcat ccggaattcc gtatggcaat gaaagacggt      240
gagctggtga tatgggatag tgttcaccct tgttacaccg ttttccatga gcaaactgaa      300
acgttttcat cgctctggag tgaataccac gacgatttcc ggcagtttct acacatatat      360
tcgcaagatg tggcgtgtta cggtgaaaac ctggcctatt tccctaaagg gtttattgag      420
aatatgtttt tcgtctcagc caatccctgg gtgagtttca ccagttttga tttaaacgtg      480
gccaatatgg acaacttctt cgcccccgtt ttcaccatgg gcaaatatta tacgcaaggc      540
gacaaggtgc tgatgccgct ggcgattcag gttggtggtg ccgtttgtga tggcttccat      600
gtcggccgta tgcttaatga actgcagcag                                       630

<210> SEQ ID NO 3
<211> LENGTH: 210
<212> TYPE: PRT
<213> ORGANISM: Artificial
<220> FEATURE:
<223> OTHER INFORMATION: Synthetic

<400> SEQUENCE: 3

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
        195                 200                 205

Gln Gln
    210

<210> SEQ ID NO 4
<211> LENGTH: 630
<212> TYPE: DNA
<213> ORGANISM: Artificial
<220> FEATURE:
<223> OTHER INFORMATION: Synthetic

<400> SEQUENCE: 4
atggagaaaa aaatcactgg atataccacc gttgatatat cccaatggca tcgtaaagaa      60
cattttgagg catttcagtc agttgctcaa tgtacctata accagaccgt tcagctggat     120
attacggcct ttttaaagac cgtaaagaaa aataagcaca gtttttatcc ggcctttatt     180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt ccctaaaggg tttattgag     420 aatatgtttt tcgtctcagc caatccctgg gtgagtttca ccagttttga tttaaacgtg     480
gccaatatgg acaacttctt cgcccccgtt ttcaccatgg caaatatta tacgcaaggc     540 gacaaggtgc tgatgccgct ggcgattcag gttcatggtg ccgtttgtga tggcttccat     600
gtcggccgta tgcttaatga actgcagcag                                     630

<210> SEQ ID NO 5
<211> LENGTH: 630
<212> TYPE: DNA
<213> ORGANISM: Artificial
<220> FEATURE:
<223> OTHER INFORMATION: Synthetic

<400> SEQUENCE: 5
atggagaaaa aaatcactgg atataccacc gttgatatat cccaatggca tcgtaaagaa      60
cattttgagg catttcagtc agttgctcaa tgtacctata accagaccgt tcagctggat     120
attacggcct ttttaaagac cgtaaagaaa aataagcaca gtttttatcc ggcctttatt     180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt ccctaaaggg tttattgag     420 aatatgtttt tcgtctcagc caatccctgg gtgagtttca ccagtttga tttaaacgtg     480 gccaatatgg acaacttctt cgcccccgtt ttcaccatgg caaatatta tacgcaaggc     540 gacaaggtgc tgatgccgct ggcgattcag gttcatgctg ccgtttgtga tggcttccat     600
gtcggccgta tgcttaatga actgcagcag                                     630

<210> SEQ ID NO 6
<211> LENGTH: 630
<212> TYPE: DNA
<213> ORGANISM: Artificial
<220> FEATURE:

-continued

<223> OTHER INFORMATION: Synthetic

<400> SEQUENCE: 6

```
atggagaaaa aaatcactgg atataccacc gttgatatat cccaatggca tcgtaaagaa      60
cattttgagg catttcagtc agttgctcaa tgtacctata accagaccgt tcagctggat     120
attacggcct ttttaaagac cgtaaagaaa aataagcaca gttttatcc ggcctttatt      180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt tccctaaagg gtttattgag     420
aatatgtttt tcgtctcagc caatccctgg gtgagtttca ccagtttga tttaaacgtg      480
gccaatatgg acaacttctt cgcccccgtt ttcaccatgg gcaaatatta tacgcaaggc     540
gacaaggtgc tgatgccgct ggcgattcag gttcatggtg ccgtttgtga tggcttccat     600
gtcggcagaa tgcttaatga actgcagcag                                      630
```

<210> SEQ ID NO 7
<211> LENGTH: 210
<212> TYPE: PRT
<213> ORGANISM: Artificial
<220> FEATURE:
<223> OTHER INFORMATION: Synthetic

<400> SEQUENCE: 7

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

Gly Ala Val Cys Asp Gly Phe His Val Gly Arg Met Leu Asn Glu Leu
        195                 200                 205

Gln Gln
    210
```

<210> SEQ ID NO 8

```
<211> LENGTH: 210
<212> TYPE: PRT
<213> ORGANISM: Artificial
<220> FEATURE:
<223> OTHER INFORMATION: Synthetic

<400> SEQUENCE: 8

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

Ala Ala Val Cys Asp Gly Phe His Val Gly Arg Met Leu Asn Glu Leu
        195                 200                 205

Gln Gln
    210

<210> SEQ ID NO 9
<211> LENGTH: 57
<212> TYPE: DNA
<213> ORGANISM: Artificial
<220> FEATURE:
<223> OTHER INFORMATION: Synthetic

<400> SEQUENCE: 9
tgggaactgc accgttctgg tccacgcccg cgccctcgcc cacgtccgga attcatg          57

<210> SEQ ID NO 10
<211> LENGTH: 19
<212> TYPE: PRT
<213> ORGANISM: Artificial
<220> FEATURE:
<223> OTHER INFORMATION: Synthetic

<400> SEQUENCE: 10

Trp Glu Leu His Arg Ser Gly Pro Arg Pro Arg Pro Arg Pro Arg Pro
1               5                   10                  15

Glu Phe Met

<210> SEQ ID NO 11
<211> LENGTH: 13
```

<210> SEQ ID NO 11
<211> LENGTH: 12
<212> TYPE: PRT
<213> ORGANISM: Artificial
<220> FEATURE:
<223> OTHER INFORMATION: Synthetic

<400> SEQUENCE: 11

Trp Glu Leu His Arg Ser Gly Pro Arg Pro Glu Phe Met
1               5                   10

<210> SEQ ID NO 12
<211> LENGTH: 729
<212> TYPE: DNA
<213> ORGANISM: Artificial
<220> FEATURE:
<223> OTHER INFORMATION: Synthetic

<400> SEQUENCE: 12
atggagaaaa aaatcactgg atataccacc gttgatatat cccaatggca tcgtaaagaa     60
cattttgagg catttcagtc agttgctcaa tgtacctata accagaccgt tcagctggat    120
attacggcct tttaaagac cgtaaagaaa aataagcaca agttttatcc ggcctttatt    180
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt ccctaaagg gtttattgag    420
aatatgtttt tcgtctcagc caatccctgg gtgagtttca ccagttttga tttaaacgtg    480
gccaatatgg acaacttctt cgccccccgtt ttcaccatgg gcaaatatta tacgcaaggc    540
gacaaggtgc tgatgccgct ggcgattcag gttggtggtg ccgtttgtga tggcttccat    600
gtcggccgta tgcttaatga actgcagcag tgggaactgc accgttctgg tccacgcccg    660
cgccctcgcc cacgtccgga attcatggcc ggctgcaaga acttcttttg gaaaaccttt    720
acgagctgc                                                           729

<210> SEQ ID NO 13
<211> LENGTH: 243
<212> TYPE: PRT
<213> ORGANISM: Artificial
<220> FEATURE:
<223> OTHER INFORMATION: Synthetic

<400> SEQUENCE: 13

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

```
Glu Asn Leu Ala Tyr Phe Pro Lys Gly Phe Ile Glu Asn Met Phe Phe
            130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
                195                 200                 205

Gln Gln Trp Glu Leu His Arg Ser Gly Pro Arg Pro Arg Pro Arg Pro
            210                 215                 220

Arg Pro Glu Phe Met Ala Gly Cys Lys Asn Phe Phe Trp Lys Thr Phe
225                 230                 235                 240

Thr Ser Cys

<210> SEQ ID NO 14
<211> LENGTH: 243
<212> TYPE: PRT
<213> ORGANISM: Artificial
<220> FEATURE:
<223> OTHER INFORMATION: Synthetic

<400> SEQUENCE: 14

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Trp Glu Leu His Arg Ser Gly Pro Arg Pro Arg Pro Arg Pro
    210                 215                 220

Arg Pro Glu Phe Met Ala Gly Cys Lys Asn Phe Phe Trp Lys Thr Phe
225                 230                 235                 240

Thr Ser Cys
```

```
<210> SEQ ID NO 15
<211> LENGTH: 42
<212> TYPE: DNA
<213> ORGANISM: Artificial
<220> FEATURE:
<223> OTHER INFORMATION: Synthetic

<400> SEQUENCE: 15
gctggctgca agaatttctt ctggaagact ttcacatcct gt                         42
```

METHODS FOR ENHANCED SOMATOSTATIN IMMUNOGENICITY IN THE TREATMENT OF OBESITY

RELATED APPLICATIONS

This application is a 35 U.S.C. §371 national phase application of PCT/US2009/048429 filed on Jun. 24, 2009, entitled "Compositions and Methods for Enhanced Somatostatin Immunogenicity in the Treatment of Growth Hormone and Insulin-Like Growth Factor One Deficiency", which application claims the benefit of U.S. Provisional Application Ser. No. 61/075,656, filed Jun. 25, 2008, entitled "Compositions and Methods for Enhanced Somatostatin Immunogenicity in the Treatment of Growth Hormone Deficiency", both of which are incorporated herein by reference in their entirety.

Incorporated by reference herein in its entirety is the Sequence Listing entitled "Sequence_Listing_as_Filed_2009_07_21_ST25.txt", created Jul. 21, 2009, size of 16.1 kilobytes.

TECHNICAL FIELD

The present invention relates to treatments of patients having growth hormone (GH) and/or insulin-like growth factor 1 (IGF-1) deficiency. More particularly, the invention relates to treatments, and the compositions and methods involved in said treatments, for patients having GH and/or IGF-1 deficiency through use of somatostatin-based antigen/adjuvant vaccines.

BACKGROUND

Prevention of infectious disease using vaccines has been in practice since the late 1700s (smallpox vaccine of 1798), including use of vaccines for prevention of polio, hepatitis B, and influenza. More recently, vaccines have also been identified for use in treatment of cancer, where the vaccine coaxes the patient's immune system into identifying and destroying target tumor cells, i.e., treatment of breast cancer, colon cancer, skin cancer, etc. Other new and useful targets for vaccine treatment are being developed due to the advantage of using a patient's own immune system to defeat the invading or cancerous agent. In most instances, a vaccine combines an antigen against which the immunity is sought and an adjuvant to enhance the response to that antigen by the recipient of the vaccine.

Growth hormone is a 191 amino acid polypeptide hormone synthesized and released from the anterior pituitary gland. Growth hormone is generally considered an anabolic hormone, required for growth/height in children, increase in calcium retention (bone strength), promotion of lipolysis, increase in protein synthesis, promotion of gluconeogenesis in the liver and other like functions. Patients who suffer from endogenous growth hormone deficiency often have poor bone density, diminished lean body mass, reduced energy, and other like general symptoms.

Presently, patients suffering from growth hormone deficiency are treated with growth hormone replacement, typically using a recombinant growth hormone expressed in genetically engineered bacteria. These treatment protocols are typically extremely costly (estimates range from $10,000 to $30,000 a year) and rely on exogenous replacement of the hormone (daily injections are typical, often spanning 18 months to the lifetime of the patient). As a result, novel, non-exogenous, long-acting, and less costly therapies are required for patients suffering from growth hormone deficiency.

In addition, therapies are also needed to treat patients in need of additional, above baseline levels, of growth hormone, for example these patients often require additional growth hormone for the treatment of obesity, wound healing, burn healing, etc.

The present invention is directed toward overcoming one or more of the problems discussed above.

SUMMARY OF THE EMBODIMENTS

Embodiments of the present invention provide compositions and methods for treatment of a growth hormone deficiency. For purpose of the invention, a growth hormone deficiency is any decrease in levels of growth hormone associated with a disease state or growth failure due to lack of adequate endogenous growth hormone secretions and/or levels. Growth hormone deficiency also includes situations where a normal endogenous level (for that patient) of growth hormone exists, but additional growth hormone is believed advantageous for the treatment of a disease or condition, for example, treatment of obesity, treatment of wounds, and treatment of burns.

Embodiments of the present invention also provide compositions and methods for treatment of an insulin-like growth factor 1 deficiency. For purpose of the invention, an insulin-like growth factor 1 deficiency is any decrease in levels of insulin-like growth factor 1 associated with a disease state or condition due to lack of adequate endogenous insulin-like growth factor 1 secretions and/or levels. Insulin-like growth factor 1 deficiency also includes situations where a normal endogenous level of insulin-like growth factor 1 exists, but additional insulin-like growth factor 1 is believed advantageous for the treatment of a disease or condition, for example, growth failure, types 1 and 2 diabetes, and cartilage repair and/or replacement.

In one embodiment, methods are provided for treatment of a growth hormone deficiency in a patient in need thereof. Methods include administering an immunogenic amount of a somatostatin-based antigen vaccine of the invention to a patient and monitoring the patient's progress. Additional vaccinations can be administered to facilitate treatment of the patient's growth hormone deficiency. Patients in need of such treatment include: adult and children that have: a lack of endogenous growth hormone that results in insufficient growth, congenital heart conditions or other like cardiac diseases, obesity, patients in need of enhanced burn repair, and patients in need of enhanced wound healing.

In another embodiment, methods are provided for treatment of an insulin-like growth factor 1 deficiency in a patient in need thereof. Methods include administering an immunogenic amount of a somatostatin-based antigen vaccine of the invention to a patient and monitoring the patient's progress. Additional vaccinations can be administered to facilitate treatment of the patient's insulin-like growth factor 1 deficiency. Patients in need of such treatment include: infants that have retinopathy of prematurity (ROP), adults and/or children that are obese, adults and/or children that have type 1 or 2 diabetes, adults and/or children that have Rett's syndrome, dogs and/or cats that are obese, horses that require replacement and/or repair of cartilage, and other like treatments.

The present invention also provides novel polypeptides, and the polynucleotides that encode them, having enhanced immunogenicity of somatostatin for use in treatment of a patient having a growth hormone or insulin-like growth factor 1 deficiency. Polypeptides of the invention include somatostatin-14 fused to an inactivated chloramphenicol acetyl transferase protein via a functionally optimized linker. Polypeptides of the invention are useful in all vertebrae species due to the highly conserved nature of somatostatin-14, stable for long term storage, highly immunogenetic, and resistant to degradation in the patient. As such, the chimeric polypeptides of the invention provide highly effective and low cost materials for use in treatment of growth hormone and/or insulin-like growth factor 1 deficiency in all vertebrae.

The present invention also provides novel adjuvants for use in the treatment of a patient in need of an immunogenic response, especially in relation to a patient in need of a treatment of either a growth hormone or insulin-like growth factor deficiency. Novel adjuvants herein are highly effective and safe for use in vertebrates, including humans, dogs, horses, cats, and the like.

The present invention also provides novel vaccines for use in the treatment of a patient having either a growth hormone or insulin-like growth factor deficiency. Vaccines are highly effective and safe for use in vertebrates, including humans, dogs, horses, cats and the like.

These and various other features and advantages of the invention will be apparent from a reading of the following detailed description and a review of the appended claims.

Figure 1:
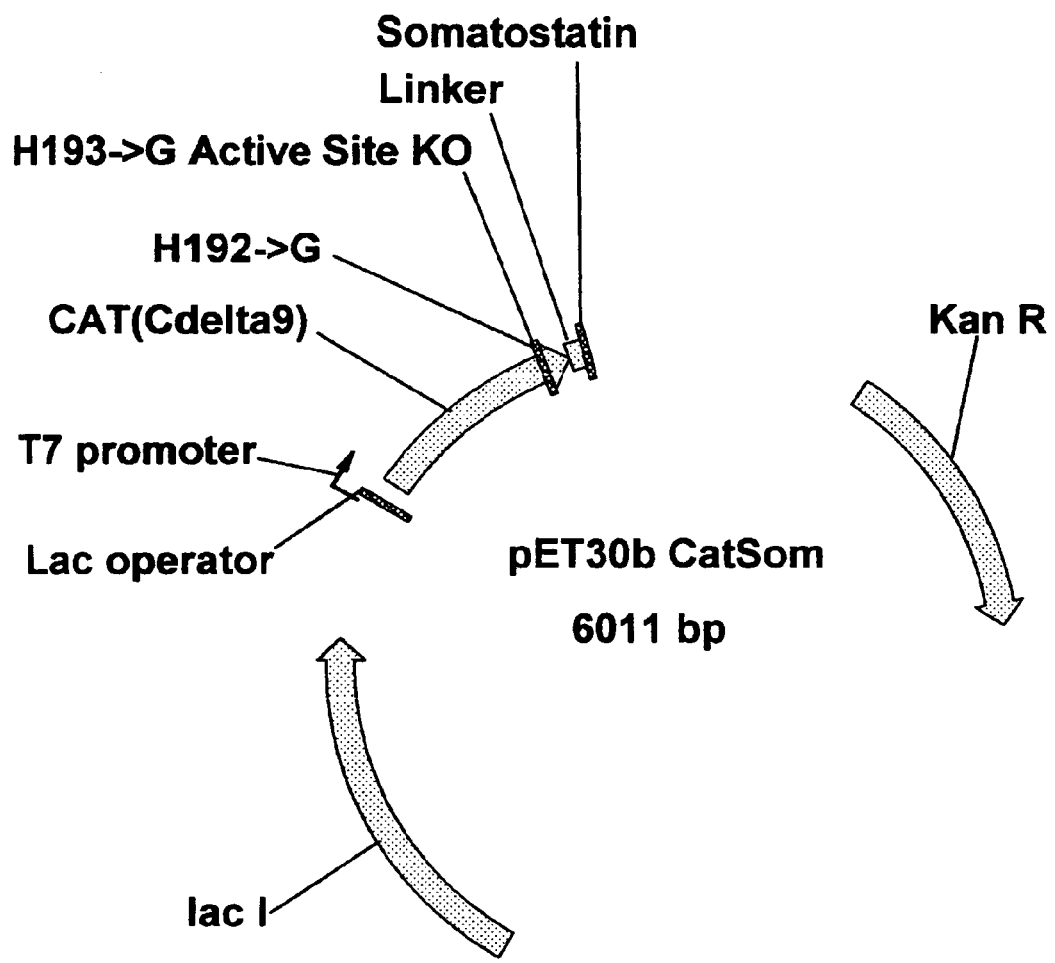
FIG. 1 is an illustrative schematic of a pET30b CatSom plasmid in accordance with embodiments of the present invention. The plasmid includes a Kanamycin resistance marker, a Lac operator, T7 promoter, CAT coding sequence all in accordance with embodiments of the invention, a linker region in accordance with the invention herein and a somatostatin encoding region in accordance with the invention are also included.

IDENTIFICATION OF SEQUENCES AND
SEQUENCE IDENTIFIERS

SEQ ID NO: 1
AGCKNFFWKTFTSC

SEQ ID NO: 15
GCTGGCTGCAAGAATTTCTTCTGGAAGACTTTCACATCCTGT

SEQ ID NO: 2 (His192->Gly, His193->Gly):
Atggagaaaaaaatcactggatataccaccgttgatatatcccaatgg
catcgtaaagaacattttgaggcatttcagtcagttgctcaatgtacc
tataaccagaccgttcagctggatattacggcctttttaaagaccgta
aagaaaaataagcacaagttttatccggcctttattcacattcttgcc -continued cgcctgatgaatgctcatccggaattccgtatggcaatgaaagacggt
gagctggtgatatgggatagtgttcacccttgttacaccgttttccat
gagcaaactgaaacgttttcatcgctctggagtgaataccacgacgat
ttccggcagtttctacacatatattcgcaagatgtggcgtgttacggt
gaaaacctggcctatttccctaaagggtttattgagaatatgtttttc
gtctcagccaatccctgggtgagtttccaccagtttttgatttaaacgtg
gccaatatggacaacttcttcgccccgttttcaccatgggcaaatat
tatacgcaaggcgacaaggtgctgatgccgctggcgattcaggttggt
ggtgccgtttgtgatggcttccatgtcggccgtatgcttaatgaactg
cagcag SEQ ID NO: 3: (His192->Gly, His193->Gly):
Mekkitgyttvdisqwhrkehfeafqsvaqctynqtvqlditaflktv
kknkhkfypafihilarlmnahpefrmamkdgelviwdsvhpcytvfh
eqtetfsslwseyhddfrqflhiysqdvacygenlayfpkgfienmff
vsanpwvsftsfdlnvanmdnffapvftmgkyytqgdkvlmplaiqvg
gavcdgfhvgrmlnelqq SEQ ID NO: 4 (His193->Gly)
Atggagaaaaaaatcactggatataccaccgttgatatatcccaatgg
catcgtaaagaacattttgaggcatttcagtcagttgctcaatgtacc
tataaccagaccgttcagctggatattacggcctttttaaagaccgta
aagaaaaataagcacaagttttatccggcctttattcacattcttgcc
cgcctgatgaatgctcatccggaattccgtatggcaatgaaagacggt
gagctggtgatatgggatagtgttcacccttgttacaccgttttccat
gagcaaactgaaacgttttcatcgctctggagtgaataccacgacgat
ttccggcagtttctacacatatattcgcaagatgtggcgtgttacggt
gaaaacctggcctatttccctaaagggtttattgagaatatgtttttc
gtctcagccaatccctgggtgagtttccaccagtttttgatttaaacgtg
gccaatatggacaacttcttcgccccgttttcaccatgggcaaatat
tatacgcaaggcgacaaggtgctgatgccgctggcgattcaggttcat
ggtgccgtttgtgatggcttccatgtcggccgtatgcttaatgaactg
cagcag SEQ ID NO: 5 (1 His193->Ala)
Atggagaaaaaaatcactggatataccaccgttgatatatcccaatgg
catcgtaaagaacattttgaggcatttcagtcagttgctcaatgtacc
tataaccagaccgttcagctggatattacggcctttttaaagaccgta
aagaaaaataagcacaagttttatccggcctttattcacattcttgcc
cgcctgatgaatgctcatccggaattccgtatggcaatgaaagacggt
gagctggtgatatgggatagtgttcacccttgttacaccgttttccat
gagcaaactgaaacgttttcatcgctctggagtgaataccacgacgat
ttccggcagtttctacacatatattcgcaagatgtggcgtgttacggt
gaaaacctggcctatttccctaaagggtttattgagaatatgtttttc
gtctcagccaatccctgggtgagtttccaccagtttttgatttaaacgtg
gccaatatggacaacttcttcgccccgttttcaccatgggcaaatat
tatacgcaaggcgacaaggtgctgatgccgctggcgattcaggttcat
gctgccgtttgtgatggcttccatgtcggccgtatgcttaatgaactg
cagcag SEQ ID NO: 6 (1 His + CAT wt)
Atggagaaaaaaatcactggatataccaccgttgatatatcccaatgg
catcgtaaagaacattttgaggcatttcagtcagttgctcaatgtacc
tataaccagaccgttcagctggatattacggcctttttaaagaccgta
aagaaaaataagcacaagttttatccggcctttattcacattcttgcc
cgcctgatgaatgctcatccggaattccgtatggcaatgaaagacggt
gagctggtgatatgggatagtgttcacccttgttacaccgttttccat
gagcaaactgaaacgttttcatcgctctggagtgaataccacgacgat
ttccggcagtttctacacatatattcgcaagatgtggcgtgttacggt
gaaaacctggcctatttccctaaagggtttattgagaatatgtttttc
gtctcagccaatccctgggtgagtttccaccagtttttgatttaaacgtg
gccaatatggacaacttcttcgccccgttttcaccatgggcaaatat
tatacgcaaggcgacaaggtgctgatgccgctggcgattcaggttcat
ggtgccgtttgtgatggcttccatgtcggcagaatgcttaatgaactg
cagcag SEQ ID NO: 7 (one H->G):
Mekkitgyttvdisqwhrkehfeafqsvaqctynqtvqlditaflktv
kknkhkfypafihilarlmnahpefrmamkdgelviwdsvhpcytvfh
eqtetfsslwseyhddfrqflhiysqdvacygenlayfpkgfienmff
vsanpwvsftsfdlnvanmdnffapvftmgkyytqgdkvlmplaiqvh
gavcdgfhvgrmlnelqq SEQ ID NO: 8: (H->A)
Mekkitgyttvdisqwhrkehfeafqsvaqctynqtvqlditaflktv
kknkhkfypafihilarlmnahpefrmamkdgelviwdsvhpcytvfh
eqtetfsslwseyhddfrqflhiysqdvacygenlayfpkgfienmff
vsanpwvsftsfdlnvanmdnffapvftmgkyytqgdkvlmplaiqvh
aavcdgfhvgrmlnelqq -continued SEQ ID NO: 9
tgggaactgcaccgttctggtccacgcccgcgccctcgcccacgtccg
gaattcatg SEQ ID NO: 10
welhrsgprprprprpefm SEQ ID NO: 11
welhrsgp(rp)$_n$efm where n > 1

SEQ ID NO: 12
Atggagaaaaaaatcactggatataccaccgttgatatatcccaatgg
catcgtaaagaacattttgaggcatttcagtcagttgctcaatgtacc
tataaccagaccgttcagctggatattacggccttttttaaagaccgta
aagaaaaataagcacaagttttatccggcctttattcacattcttgcc
cgcctgatgaatgctcatccggaattccgtatggcaatgaaagacggt
gagctggtgatatgggatagtgttcaccctcgttacaccgttttccat
gagcaaactgaaacgttttcatcgctctggagtgaataccacgacgat
ttccggcagtttctacacatatattcgcaagatgtggcgtgttacggt
gaaaacctggcctatttccctaaagggtttattgagaatatgttttttc
gtctcagccaatccctgggtgagtttcaccagttttgatttaaacgtg
gccaatatggacaacttcttcgcccccgttttcaccatgggcaaatat
tatacgcaaggcgacaaggtgctgatgccgctggcgattcaggttggt
ggtgccgtttgtgatggcttccatgtcggccgtatgcttaatgaactg
cagcagtgggaactgcaccgttctggtccacgcccgcgccctcgccca
cgtccggaattcatggccggctgcaagaacttcttttggaaaacccttt
acgagctgc SEQ ID NO: 13
mekkitgyttvdisqwhrkehfeafqsvaqctynqtvqlditaflktv
kknkhkfypafihilarlmnahpefrmamkdgelviwdsvhpcytvfh
eqtetfsslwseyhddfrqflhiysqdvacygenlayfpkgfienmff
vsanpwvsftsfdlnvanmdnffapvftmgkyytqgdkvlmplaiqvg
gavcdgfhvgrmlnelqqwelhrsgprprprprpefmagcknffwktf
tsc SEQ ID NO: 14
mekkitgyttvdisqwhrkehfeafqsvaqctynqtvqlditaflktv
kknkhkfypafihilarlmnahpefrmamkdgelviwdsvhpcytvfh
eqtetfsslwseyhddfrqflhiysqdvacygenlayfpkgfienmff
vsanpwvsftsfdlnvanmdnffapvftmgkyytqgdkvlmplaiqvh
havcdgfhvgrmlnelqqwelhrsgprprprprpefmagcknffwktf
tsc

DETAILED DESCRIPTION

The present invention provides compositions and methods for treatment of growth hormone deficiency in patients in need of such treatment. For purposes herein, and as described previously, a growth hormone deficiency is any decrease in levels of growth hormone associated with a disease state or condition due to lack of adequate endogenous growth hormone secretions and/or levels in the patient. Growth hormone deficiency also includes situations where a normal endogenous level of growth hormone exists, i.e., normal for the patient, but additional growth hormone is believed advantageous to the patient for the treatment of a target disease or condition, for example, treatment of obesity, treatment of wounds, treatment of burns, etc.

The present invention also provides compositions and methods for treating insulin-like growth factor deficiency 1 in patients in need of such treatment. For purposes herein, an insulin-like growth factor 1 deficiency is any deficiency in levels of insulin-like growth factor associated with a disease state due to lack of adequate endogenous insulin-like growth factor 1 secretions. Insulin-like growth factor 1 deficiency also includes situations where a normal level of insulin-like growth factor exists, i.e., normal for the patient, but additional factor 1 is advantageous to the patient for the treatment of a disease or condition, for example, obesity, type 1 and 2 diabetes, and Rett's syndrome.

In one embodiment, novel polypeptides, and the polynucleotides that encode them, are provided including polypeptides of somatostatin-14 fused to an inactivated chloramphenicol acetyl transferase protein via a functionally optimized linker. The chimeric polypeptides of the invention provide highly effective and low cost materials for use in treatment of growth hormone and/or insulin-like growth factor 1 deficiency.

In another embodiment, novel adjuvant compositions are provided for use in treatment of patient's having growth hormone and/or insulin-like growth factor 1 deficiency. In one particular embodiment, somatostatin-based antigen can be combined with novel adjuvants and used in the treatment of growth hormone or insulin-like growth factor 1 deficiency related disease states or conditions, e.g., growth deficiency in children, growth deficiency in adults, lack of adequate endogenous growth hormone secretions, healing of burns, obesity, cardiac disease, etc. Adjuvants herein are designed for optimal use in vertebrates, and in particular humans. Adjuvants herein provide for enhanced immunogenicity over conventional adjuvants, thereby allowing for vaccines to include smaller quantities of antigen. Adjuvant embodiments herein are useful with other antigen combinations beyond those useful in the treatment of growth hormone and/or insulin-like growth factor 1 deficiencies. Novel stand-alone adjuvant embodiments are therefore within the scope of the present invention but adjuvants herein will predominately be described in accordance with somatostatin-based antigen.

In yet another embodiment, vaccines are provided that result in immunogenicity against somatostatin that results in diminution of somatostatin and thereby removal of a proportion of the inhibition that somatostatin exerts on growth hormone release and thereby insulin-like growth factor 1 release. Vaccine embodiments herein are optimized for both safety and function, having highly immunogenic somatostatin constructs in safe and highly effective adjuvant compositions. Vaccines of the present invention require relatively smaller amounts of antigen (as compared to conventional vaccines), have enhanced storage life, and are lower cost.

Although the present invention is targeted at treatment of growth hormone and/or insulin-like growth factor 1 deficiency in humans, treatment of these deficiencies in other vertebrates is contemplated to be within the scope of the present invention. For example, dogs and cats showing signs of obesity, and horses needing repair or replacement of cartilage can be treated using the compositions and methods described herein.

The following definitions are provided to facilitate understanding of certain terms used frequently herein and are not meant to limit the scope of the present disclosure.

DEFINITIONS

"Amino acid" refers to any of the twenty naturally occurring amino acids as well as any modified amino acid sequences. Modifications may include natural processes such as posttranslational processing, or may include but are not limited to phosphorylation, ubiquitination, acetylation, glycosylation, covalent attachment of flavin, ADP-ribosylation, cross-linking, iodination, methylation, and the like.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the definition of antibody in accordance with the present invention.

"Isolation" refers to a polynucleotide or polypeptide that has been separated or recovered from at least one contaminant of its natural environment. In some cases the polynucleotide or polypeptides have been separated or recovered from 10%, 20%, 30%, 40%, 50%, 60%, 70%, 80%, 90%, 95%, 96%, 97%, 98%, 99% or 100% of contaminants of its natural environment. Ordinarily, isolated polynucleotides or polypeptides are prepared using at least one purification step. In this regard, purify or purification, refers to a target polypeptide free from at least 5%, 10%, 20%, 30%, 40%, 50%, 60%, 70%, 80%, 90% 95%, 96%, 97% 98% or 99% of the contaminating polypeptides. Purification of a polypeptide from contaminating polypeptides can be accomplished through any number of well known techniques, including ammonium sulfate or ethanol precipitation, anion or cation exchange chromatography, phosphocellulose chromatography, hydrophobic interaction chromatography, affinity chromatography, hydroxylapatite chromatography, and lectin chromatography.

"Obesity" refers to a subject being at least 20% over an ideal body weight. For a human, for example, ideal body weight is determined by the subject's height, age, sex and build. Obesity herein includes the terms: mildly obese (20-40% over ideal weight), moderately obese (40-100% over ideal weight) and severely obese (over 100% of ideal weight).

"Patient" refers to a vertebrate, typically a mammal, in need of the compositions and/or methods of the present invention, for example a human in need of weight loss (obese, for example) or horse in need cartilage repair.

"Percent" nucleic acid or amino acid sequence identity describes the percentage of nucleic acid sequence or amino acid residues that are identical with a reference polynucleotide or polypeptide. In some instances, sequences are aligned and gaps introduced to achieve maximum sequence identity. In some instances a computer program is employed to calculate percent identity, for example, Gap program (Wisconsin Sequence Analysis package, Version 8 for Unix, Genetics Computer Group, University Research Park, Madison Wis.), that uses an algorithm of Smith and Waterman, 1981, Adv. Appl. Math., 2:482-489 (each of which is incorporated by reference in their entirety herein) or ALIGN-2 sequence comparison computer program (see WO 00/15796).

"Polynucleotide" refers to a linear sequence of nucleotides. The nucleotides are either linear sequence of polyribonucleotides or polydeoxyribonucleotides, or a mixture of both. Examples of polynucleotides in the context of the present invention include—single and double stranded DNA, single and double stranded RNA, and hybrid molecules that have both mixtures of single and double stranded DNA and RNA. Polynucleotides also includes one or more modified nucleotides and peptide nucleic acids (PNA).

"Protein," "peptide," and "polypeptide" are used interchangeably to denote an amino acid polymer or a set of two or more interacting or bound amino acid polymers.

"Treatment" or "treating" refers to improvement of a subject relative to an untreated subject in a relatively identical situation. Treatment or treating generally indicates that a desired pharmacological and/or physiological effect has been achieved using the compositions and methods of the present invention. Treatment or treating can include prophylactic treatments.

"Vaccine" refers to any composition that can stimulate the vaccinated subject's immune system to produce antibodies for the purposes described herein.

Growth Hormone

Growth hormone is a 191 amino acid peptide produced and released from somatotroph cells in the anterior pituitary. Growth hormone levels in the body are regulated by growth hormone releasing hormone (GHRH) and somatostatin. GHRH results in synthesis and release of growth hormone (stress, exercise, etc. are also known stimulators of growth hormone release) while somatostatin inhibits the release of growth hormone.

Growth hormone (GH) is generally involved in a variety of physiologic functions in the body, including: increase of height throughout childhood, increase of muscle mass through sarcomere hyperplasia, promoting lipolysis, promoting gluconeogenesis in the liver, and involvement in fuel homeostasis. Growth hormone deficiencies typically manifest themselves in a number of known disease or physiologic states, including: short stature/growth failure if the deficiency occurs during childhood, strength deficits, loss of bone mass, increase in cardiovascular risks, e.g., chronic heart failure (Tien et al., Growth Hormone: A Promising Treatment for the Failing Heart, 2000, Pharmacotherapy 20(9):1096-1106, incorporated herein by reference in its entirety), and other like states. In addition, supplemental growth hormone to a subject is potentially useful in the treatment of wounds, burns, obesity, and the like. Vickers et al., 2002, Adult growth hormone treatment reduces hypertension and obesity induced by an adverse prenatal environment, J. Endocrinol, 175(3):615-623; Ramirez et al., 1998, Is there a role for growth hormone in the clinical management or burn injuries, Growth Hormone IGF Res. Suppl. B:99-105; and Lal et al., 2000, Growth hormone, burns and tissue healing, Growth Hormone IGF Res. 10 Suppl. B:539-543, each of which is incorporated by reference herein for all purposes.

Conventional therapies for combating growth hormone deficiency include supplementation to the afflicted individual with recombinant human growth hormone (see, for example, U.S. Pat. Nos. 4,446,235 and 4,601,980). Growth hormone supplementation therapies typically require subcutaneous injection of recombinant growth hormone on a continual basis, i.e., daily injections for at least 18 months is typical, although a significant number of individuals require lifetime treatment. Recently, growth hormone supplementation therapies have been used in treatment of Multiple sclerosis (MS), treatment of fibromyalgia, treatment of Crohn's disease and/or ulcerative colitis, treatment to reverse effects of aging, treatment of burns, and treatment for idiopathic short stature. However, treatment with recombinant growth hormone therapy has been shown to potentially increase the risk of diabetes, colon cancer, etc. In addition, treatment of a patient with a recombinant protein is typically lacking in internal feed-back controls providing an environment of constant monitoring and patient care, with increase risks associated when the patient has an active malignancy. Further, recombinant growth hormone is extremely expensive to procure, and costs of use over the course of one or more years can be prohibitive, as are the regiment of daily administrations via injection. As such, embodiments of the present invention provide an unexpected and substantial benefit in treatment of these growth hormone deficiency related diseases or conditions.

Insulin-Like Growth Factor 1 (IGF-1)

IGF-1 is a polypeptide protein hormone similar in structure to insulin. IGF-1 is produced in the liver and other target tissues in response to growth hormone and generally has anabolic effects upon release. Typically, IGF-1 acts through the AKT signaling pathway (AKT representing a family of serine/threonine-specific protein kinases). Generally, IGF-1 anabolic effects include cell growth and multiplication as well as an inhibition of apoptosis at target sites.

A number of factors are involved in influencing IGF-1 levels in a patient's circulation, including: level of growth hormone, genetic make-up, time of day, age, gender, exercise status, stress, body mass index, and disease state. IGF-1 deficiency can be characterized by growth retardation or failure, and is associated with several conditions, including: obesity, types 1 and 2 diabetes, cardiovascular disease, various stress disorders, and the like.

Recombinant IGF-1 has been used in the treatment of several of these maladies, with mixed results. Presently, Increlex® (a recombinant IGF-1 produced by Tercica) is available in the United States for treatment of target disorders, although clinical results have varied.

Somatostatin

Somatostatin is a peptide hormone that inhibits, among other things, release of growth hormone from the anterior pituitary. Somatostatin regulates various endocrine functions via interaction with G-protein-coupled somatostatin receptors on target endocrine cells. Somatostatin is secreted from sites in the hypothalamus, stomach, intestine and pancreas. Control of somatostatin levels in a target animal has most recently been identified as a point of interest for increasing productivity of farm animals, i.e., control of somatostatin levels enhances dairy cow milk production or a farm animals' size, etc (see co-pending application Ser. No. 12/198,579, entitled Chloramphenicol Acetyl Transferase (CAT)-Defective Somatostatin Fusion Protein And Uses Thereof, which is incorporated herein by reference for all purposes).

In these studies, productivity of farm animals was optimized through use of vaccination protocols with somatostatin antigens. In general, farm animals immunized with somatostatin had an average daily weight gain of 10-20%, an appetite reduced by 9% and an 11% increase in the efficiency of food utilization. Animals immunized with somatostatin, and also their offspring have correct proportions, and the distribution of the weight of the animals between the muscles, bones and fat is the same as in control animals (see Reichlin, 1987). However, alternative somatostatin treatments, for example, direct treatment of target animals with anti-somatostatin antibodies, have proven to be overly costly and functionally less-dramatic, thereby eliminating direct antibody treatment as non-practical. Muromtsev G. S., et al., 1990, Basics of agricultural biotechnology, Agropromizdat, Moscow, pp 102-106. These studies, therefore, indicate that inducing somatostatin immunogenicity in a target animal can accomplish safe and effective results.

The inventor's herein have realized the surprising and unexpected result that modification of these vaccination protocols (including methods and compositions therein) can be used in treatment of human disease or physiologic states, and in particular, treatment of human growth hormone and/or IGF-1 deficiency.

Embodiments of the present invention provide somatostatin-based treatments for growth hormone deficiency in vertebrates, and, more particularly, in mammals. Typical embodiments are directed at treatments in humans, dogs, cats and horses. Humans and other mammals immunized with somatostatin are treated with vaccines of the invention (see below) to limit or inhibit the effects that native somatostatin has on growth hormone release. For example, where recombinant growth hormone would be administered to a patient deficient in growth hormone or in need of excess growth hormone, for treatment of burns, cardiac therapy, diabetes, etc, vaccines of the invention would be provided to result in additional endogenous growth hormone release. Vaccine antigens and adjuvants are optimized for vertebrates use and in particular human use and disease treatment. Since somatostatin is highly conserved in vertebrates, embodiments of the present invention are useful in eliciting an immune response in all target vertebrates vaccinated using methods and compositions herein. A significant benefit of the present invention is that vaccinated patients can go weeks to months between booster events, allowing the patient's immune system to limit or eliminate somatostatin from the system.

Embodiments of the present invention also provide somatostatin-based treatments for IGF-1 deficiency in vertebrae, and in particular in mammals, e.g., humans, dogs, cats, horses, and the like. Vertebrae immunized with vaccines of the invention limit or inhibit the effects somatostatin has on IGF-1 levels in that animal. Treatment embodiments can be used to treat any number of diseases and/or conditions associated with IGF-1 deficiency or where additional IGF-1 is required to improve the treated animal's health or condition.

As such, aspects of the present invention facilitate somatostatin based immunization vaccines by providing highly immunogenic materials for use in prevention and treatment of disease and/or other conditions. These somatostatin based immunization compounds have been optimized for expression and antigenicity.

In some embodiments, somatostatin-14 is expressed as a codon-optimized, CAT-deficient somatostatin chimeric polypeptide. These materials provide an unexpected therapeutic for use in treatment of growth hormone and IGF-1 deficiency based diseases as well as where additional levels of either growth hormone or IGF-1 would be useful in a treatment regimen. As described more fully below, the present invention also provides optimized adjuvants for maximizing the effects of the codon-optimized, CAT-deficient somatostatin chimeric polypeptides. Somatostatin-based antigens of the invention are designed to provide larger size molecules (27,000+ Daltons vs. 1,600 for native somatostatin), immunogenicity and resistance to degradation. In this manner a somatostatin-based antigen of the invention is present longer (longer ½ life in the patient), with greater effect (greater immunogenicity), in a treated patient. These novel antigens for use in vertebrates provide optimal exposure for a patients' immune system to respond.

Novel Vaccine Embodiments for Use in Treatment of Growth Hormone Deficiency

Somatostatin has two active forms that are produced by alternative cleavage of a polypeptide. Costoff A. Section 5, Chapter 4: Structure, Synthesis, and Secretion of Somatostatin. Endocrinology: The Endocrine Pancreas. Medical College of Georgia, page 16, incorporated by reference in its entirety for all purposes. Although it is contemplated that either somatostatin form can be used in somatostatin-based antigen embodiments herein, somatostatin-14 will be described in detail. Somatostatin-14 is a biologically active tetradecapeptide produced in the hypothalamus and gastrointestinal tract (stomach, intestine, and pancreas). The amino acid sequence of the tetradecapeptide is AGCKNFF-WKTFTSC (SEQ ID NO: 1). The sequence of somatostatin-14 is highly conserved among vertebrates (Lin X W et al. Evolution of neuroendocrine peptide systems: gonadotropin-releasing hormone and somatostatin. Comp. Biochem. Physiol. C. Pharmacol. Toxicol. Endocrinol. 1998 119(3): 375-88.) The tetradecapeptide is encoded by a nucleic acid sequence: GCTGGCTGCAAGAATTTCTTCTGGAA-GACTTTCACATCCTGT (SEQ ID NO: 15) (note that other nucleic acid sequences can be used to code SEQ ID NO:1, however, SEQ ID NO: 15 is provided for illustrative purposes).

Somatostatin-14 is known to have strong inhibitory effect on a large number of hormones involved in the growth and utilization of food in animals. As previously described in U.S. Pat. No. 6,316,004 and U.S. patent application Ser. No. 12/198,579 (each incorporated herein by reference for all uses), somatostatin and chimeric versions of somatostatin can be used in immunization of animals for increase in daily weight and, where appropriate, milk production. These immunization procedures were performed with conventional adjuvants. Somatostatin-14 immunization has not been used in the treatment of any particular growth hormone deficiency state.

One aspect of the invention provides isolated nucleic acid molecules that encode chimeric proteins having optimized somatostatin immunogenic activity. In particular, embodiments of the invention include novel nucleic acid constructs that encode CAT fusion proteins having immunogenic activity for somatostatin. These polypeptides have been identified for optimal functional activity in immunization procedures and use in treatment of growth hormone and/or insulin-like growth factor 1 deficiencies and in particular in treatment of mammalian growth hormone and/or insulin-like growth factor 1 deficiencies.

In one embodiment, a construct having a schematic as shown in FIG. 1 is provided to encode the chimeric polypeptides of the invention. Nucleic acid constructs of the invention generally encode an inactive CAT enzyme without 10 C-terminal amino acids and includes one or two histidines replaced amino acids. The CAT enzyme is inactivated by removing the imidazole group of His193 (His195 in the canonical $CAT_{III}$ variant). In another embodiment the CAT enzyme is inactivated by removing the imidazole groups of both His 193 and the nearby His192 (respectively His195 and His194 for $CAT_{III}$). Removal of the essential His193 (His195 in $CAT_{III}$) imidazole group from the active site of CAT and replacement with an alanine, glycine or other like amino acid results in substantial inactivation of the CAT enzyme (see for example, Lewendon A et al. (1994) Replacement of catalytic histidine-195 of chloramphenicol acetyl transferase: evidence for a general base role for glutamate. Biochemistry. 33(7):1944-50; White et al., (2000) Characterization of Chloramphenicol and Florfenicol Resistance in *Escherichia coli* associated with Bovine Diarrhea. J. Clin. Micro 38 (12) p 4593-4598. each of which is incorporated by reference herein for all purposes). Finally, embodiments herein can also include CAT enzyme inactivation through removal of the imidiazole group of His192 alone (His 194 for $CAT_{111}$). As for His193, replacement can be with an alanine, glycine or other like amino acid.

In some aspects, the one or more replaced histidine amino acids are encoded by nucleic acids located at position numbers 574-576 and 577-579 of SEQ ID NO: 2 (corresponding to amino acid numbers 192 and 193 in SEQ ID NO: 3). In some embodiments the nucleic acid sequences of the invention include SEQ ID NO: 4, SEQ ID NO: 5 and SEQ ID NO: 6. Chimeric proteins of the invention that include the histidine replaced constructs herein provide highly immunogenic proteins with little or no CAT activity, a significant improvement over the existing art. The inactivated CAT enzyme embodiments are attached to a somatostatin polypeptide of the invention. This attachment can be made directly or with a linker (as described more fully below).

CAT inactivation, at sites his192 and his193, can be accomplished via any number of known procedures to those skilled in the art including site-directed mutagenesis and synthetic gene assembly. In one embodiment, the nucleic acid sequence that encodes histidine 193 or histidine 192 are modified to encode an alanine, glycine or other like amino acid. In another embodiment, the nucleic acid sequences that encode both histidine 192 and 193 are modified to encode alanine, glycine or other like amino acids. Typical replacements for the 192 and 193 chimeric polypeptide include: alanine, alanine, alanine, glycine, glycine, alanine, glycine, glycine.

Embodiments of the present invention also include the amino acid sequences for CAT deficient polypeptides of the invention, including amino acid sequence having SEQ ID NO: 7, 8 and 3 (corresponding to his→gly at 193, his→ala at 193, and his→gly at both 192 and 193).

The realization that CAT enzyme could be inactivated and used as a carrier protein for presentation of somatostatin-14 in the treatment of diseases and/or conditions herein, especially in mammals, was an unexpected finding of the inventors. Non-inactivated CAT has been described as the enzyme responsible for plasmid mediated bacterial resistance for both Chloramphenicol and Florfenicol (fluorinated analogue) in multiple, worldwide, gram-negative bacterial isolates. The use of the non-inactivated CAT, as described U.S. Pat. No. 6,316,004B1, predates these scientific discoveries. As such, according to current understanding and established standards, the use of non-inactivated CAT would be counterindicated due to safety concerns (i.e., creation of more antibiotic resistant hosts). Chloramphenicol was discovered about 60 years ago and was primarily used as an antibiotic. Several health concerns arose out of this usage including recipients of the drug developing aplastic anemia. In addition, where the antibiotic fluorinated analogue continued to be used, for example in the cattle industry, an increase in several strains of bacteria becoming resistant to the antibiotic, due to plasmid encoded genes. Although Chloramphenicol continues to be used in eye drops to treat bacterial conjunctivitis, it is not used in the United States to treat other bacterial borne disease. As such, the realization and development of using an inactivated CAT enzyme in any matter in mammalian, and in particular human, is surprising, where utilization of the carrier protein based benefits described throughout this specification, while avoiding the significant health concerns of active CAT, provides significant improvement to vaccines described herein.

Note that these "carrier" related improvements of CAT for use with small molecules are discussed in co-pending and related U.S. Patent Application S/N PCT/US08/68195 as well as in U.S. Pat. No. 6,316,004 both of which are incorporated by reference herein for all purposes. In particular, the inventors herein unexpectedly found that an inactivated CAT enzyme as a carrier protein for somatostatin-14 could avoid the significant health risks associated with the enzyme while utilizing the chimeric proteins enhanced capacity for immunogenicity, resistance to enzyme degradation, increased half-life and enhanced uptake by the patient's macrophages.

As shown in FIG. 1, the non-active CAT enzyme can be linked to somatostatin-14 via a variable length linker or spacer. The spacer is required to insure presentation of the encoded somatostatin on a global surface. Spacer embodiments herein provide for optimal protease resistance and for optimal epitope exposure and have shown unexpected improvement over constructs not having the linker sequence(s) of the present invention.

Spacer embodiments, therefore, have been optimized in length and composition to ensure CAT-defective somatostatin expression in various microorganisms, and in particular in *E. Coli*. Original constructs as described in U.S. Pat. No. 6,316, 004, included a spacer having rare *E. Coli* codons and required the co-expression of rare tRNAs from a second or helper plasmid. Spacer embodiments herein remove these rare *E. Coli* codons and thereby remove the need for a second helper plasmid, an improvement over previous technology.

In typical embodiments, the spacer has a nucleic acid sequence of tgggaactgcaccgttctggtccacgc-ccgcgccctcgcccacgtccggaattcatg (SEQ ID NO: 9). One example of a spacer of the invention has an amino acid sequence of welhrsgprprprprpefm (SEQ ID NO: 10). A typical amino acid sequence for a spacer of the invention is welhrsgp(rp)$_n$efm where n>1 (SEQ ID NO: 11). As noted above, these novel spacer sequences provide for enhanced protease resistance (thereby allowing for increased production as compared to constructs disclosed in U.S. Pat. No. 6,316,004) and optimal somatostatin-14 exposure. This combination of somatostatin attaches to an inactivated CAT enzyme by an optimally configured linker show unexpected improvement when used to immunize target patients for disease treatment. These constructs are used as antigens in the treatment of growth hormone and insulin-like growth factor 1 deficiency based diseases.

Further, these chimeric constructs show enhanced storage stability as compared to somatostatin-14 alone. In addition, the somatostatin-based antigens of the present invention provide for greater half-life in the patient given the enhanced resistance to degradation in these materials. It is noted that other carrier polypeptides can replace inactivated CAT as attached to the somatostatin. For example, somatostatin-14 can be combined with KLH, tetanus toxoids or CRM instead of inactivated CAT enzyme.

Embodiments of the invention also provide novel adjuvant compositions for enhanced induction of humoral immunity in a target patient. These adjuvant compositions provide a significant improvement over conventional materials for the induction of a humoral response and are safe for use in human targets. Adjuvant compositions herein are used with somatostatin-based antigens to produce vaccines of the invention. Vaccines of the invention are then useful in the treatment of GH and/or IGF-1 deficiency-based diseases or conditions.

In embodiments herein, all components of adjuvant compositions are of non-animal origin, thereby eliminating potential cross-contamination of vaccinated humans from potentially contaminated adjuvant components. For example, embodiments herein can utilize animal origin free Tween 80. Surprisingly, animal origin free Tween 80 shows significantly better results in the use of vaccines herein as compared to animal origin Tween 80, and eliminates the possibility of animal-based contamination into the vaccine, e.g., Bovine Spongiform Encephalopathy (BSE). In addition, animal origin free Tween 80 shows better capacity to emulsify as compared to animal origin Tween 80, providing an additional unexpected benefit for its use in accordance to embodiments herein.

Adjuvant embodiments herein are also free of benzene and other like carcinogenic compounds. These embodiments provide a safety benefit not available in most conventional adjuvant compounds. For example, embodiments herein utilize Carbopol 974P or benzene free polycyclic acid.

In one embodiment, the immunologic adjuvant comprises a carbopol base, a squalene base and an arabinogalactan solution. In more detail, the Carbopol base is prepared using Carbopol 974P in water or saline. The squalene base is prepared from a combination of squalene, non-animal origin Tween 80 and Span 85. In some embodiments the squalene base is MF59 (Chiron Corp., Emeryville, Calif.). The arabinogalactan is dissolved in PBS or saline. Adjuvant compositions are combined with chimeric polypeptides of the invention to produce vaccines of the invention.

In yet another embodiment, the immunologic adjuvant comprises a Carbopol base, a squalene base and a tragacanthin solution. In more detail, the Carbopol base is prepared using Carbopol 974 P in water or saline. The squalene base is prepared from a combination of squalene, non-animal origin Tween 80 and Span 85. Purified tragacanthin is dissolved in PBS or saline. Adjuvant compositions are combined with chimeric polypeptides of the invention to produce vaccines or the invention.

Specific adjuvant combination and concentrations are shown in Example 3. Adjuvants in accordance with the present invention are safe and effective for human use, avoid animal products, avoid petroleum based hydrocarbons, and avoid carcinogenic compounds.

Vectors and Host Cells

The present invention also relates to vectors comprising the polynucleotide molecules of the invention, as well as host cells transformed with such vectors. Any of the polynucleotide molecules of the invention may be joined to a vector, which generally include a selectable marker and origin of replication, for the propagation host of interest. Host cells are genetically engineered to include these vectors and thereby express the polypeptides of the invention. Generally, vectors herein include polynucleotides molecules of the invention operably linked to suitable transcriptional or translational regulatory sequences, such as those for microbial or viral host cells. Examples of regulatory sequences include transcriptional promoters, operators, or enhancers, mRNA ribosomal binding sites, and appropriate sequences which control transcription and translation. Nucleotide sequences are operably linked when the regulatory sequences herein functionally relate to the chimeric polypeptide encoding polynucleotides of the invention.

Typical vehicles include plasmids, yeast shuttle vectors, baculovirus, inactivated adenovirus, and the like. In one embodiment the vehicle is a modified pET30b CatSom plasmid (see FIG. 1). Target host cells for use herein include bacterial host, e.g., *E. Coli.*, yeast, SF-9 insect cells, mammalian cells, green plants, and the like.

In one embodiment, the regulatory sequences include a T7lac, CAT, Trp, or T5 promoter for expression of the chimeric polypeptides of the invention in *E. coli* or other like microbes. These regulatory sequences are known in the art and are used under appropriate and known conditions.

Various plasmids of the invention have been constructed for expression of chimeric polypeptides of the invention through utilization of target regulatory sequences. Illustrative plasmids can include a T7lac promoter (see FIG. 1).

Host cells for expression of target chimeric polypeptides include prokaryotes, yeast and higher eukaryotic cells. Illustrative prokaryotic hosts include bacteria of the genera *Escherichia, Bacillus*, and *Salmonella* as well as the genera *Pseudomonas* and *Streptomyces*. In typical embodiments the host cell is of the genera *Escherichia* and can be *Escherichia Coli* (*E. coli*). Host cells (yeast or bacterial) can also be used to produce target polypeptides of the invention as virus-like particles (VLPs).

As shown in the Examples below, constructs of the invention provide for optimal CAT deficient somatostatin expression under a variety of conditions. These constructs are particularly efficient for expression in prokaryotic hosts and in particular bacteria of the genera *Escherichia*.

Endotoxin Free Fusion Protein for use in Vaccines of the Invention

Aspects of the present invention include use of endotoxin free, codon-optimized, CAT-deficient somatostatin. In one embodiment, the chimeric immunogenic somatostatin-comprising proteins of the invention are prepared by transforming target cells with appropriate somatostatin-containing vehicles. As noted above, vehicles for use herein include known plasmid and vector systems suitable for expression in selected target cells.

In an aspect of the invention, chimeric immunogenic somatostatin-comprising proteins are expressed in target host cells. Chimeric protein expression is performed using target regulatory sequences. In some aspects the chimeric polypeptides have been optimized (especially with regard to spacer sequences disclosed herein) for expression in E. Coli.

Chimeric protein can then be purified in accordance with known protein purification technologies, including, for example, lysozyme lysis, differential centrifugation of inclusion bodies, sieve chromatography and the like. Refolding procedures can be conducted in guanidine chloride and urea at alkaline pH followed by dialysis and lyophilization.

In one embodiment, E. coli cells are transformed using the codon-optimized, CAT-deficient somatostatin containing plasmid—pET30b CatSom; the pET30b CatSom having appropriate E. Coli base regulatory sequences for expression. In some cases, fermentation of approximately ten liters of these cells provides at least 500 grams and in some cases 600 grams of total biomass, yielding about 4-6 grams of total protein. It is estimated from silver and Coomassie blue staining that about half of the protein is the target chimeric protein (see Example 2 and FIG. 2).

In some embodiments herein, chimeric protein of the invention is purified from transformed host cells in a substantially endotoxin free state. Additional purification will remove or lower the endotoxin to acceptable levels for human uses according to Food and Drug Administration standards.

As such, some embodiments herein are directed at production of substantially endotoxin free chimeric proteins for use in vaccines. In certain embodiments the endotoxin levels are at or below 1 EU/ml and in other embodiments the endotoxin levels are substantially eliminated, i.e., the chimeric polypeptides of the invention are substantially endotoxin free.

In one embodiment, recovered IB from lysed host cells was washed multiple times using a wash buffer devoid of endotoxin. The recovered IP pellet can optionally be washed until endotoxin levels are below approximately 1 EU/ml (endotoxin tests can be performed using one or more known assays, including commercially available test kits from MP Biochemicals, Charles River, etc.). In some embodiments the wash buffer is endotoxin free and includes one or more proteolytic protein inhibitor(s), e.g., phenylmethanesulphonylfluoride (PMSF). In some embodiments the wash buffer is phosphate buffered saline (PBS) having an inhibitory effective amount of PMSF and/or Aminoethyl-Benzenesulfonyl Fluoride Hydrochloride (AEBSF).

In some aspects, substantially endotoxin free pellets can be treated with a protein unfolding solution at pH 12.5 containing urea and refolded in a protein refolding solution containing a reduced molarity of urea with arginine, glycerol and/or sucrose. Purified chimeric protein concentration is modified to be between 1 and 3 mg/ml and typically about 1.4 to 1.8 mg/ml. In some cases, substantially endotoxin free chimeric protein is provided to vaccine formulations at about 1.5 to 5 mg/2 ml dose and more typically from 2.0 to 3.5 mg/2 ml dose. Other endotoxin removal procedures can also be utilized, for example commercially available ion-exchange endotoxin removal columns, hydrophobic columns, etc.

Vaccines

Vaccines of the invention are combinations of immunologic adjuvants as described herein and target antigens useful in the prevention or treatment of a human disease state.

The pharmaceutical dosage for vaccine embodiment herein includes 1-5 mg chimeric polypeptide. In all embodiments herein the vaccine should be sterile, fluid and stable under conditions of manufacture and storage. The prevention of the action of microorganisms can be accomplished by addition of various antibacterial and antifungal agents, for example, parabens, chlorobutanol, sorbic acid, thimerosal and the like.

Vaccines herein typically include an antigen in a total protein amount of from about 1 mg/2 ml to 3 mg/2 ml dose, wherein approximately 5% to 25% of the dose is adjuvant and more typically from about 10% to 20% of the dose is adjuvant. In some embodiments the adjuvant makes-up about 18% of the dose.

For purposes of illustration, the adjuvants of the invention are combined with a somatostatin based polypeptide to provide a vaccine useful in the treatment of human growth hormone and/or insulin-like growth factor 1 deficiency based diseases and/or conditions. Note that the adjuvants described herein could be combined with other antigens to produce novel vaccines useful in the treatment of other target human disease.

Method for Treatment of Human Disease

The invention provides pharmaceutical grade vaccines containing chimeric polypeptides and adjuvants of the invention. Such vaccines can be administered to patients having a growth hormone and/or insulin-like growth factor 1 deficiency to facilitate appropriate release from endogenous sources in the patient.

Vaccines of the invention are provided to patients having a growth hormone and/or insulin-like growth factor 1 deficiency. In one embodiment, vaccines of the invention provided 1 to 2 times, with 3 to 5 boosters over the course of a treatment. A typical vaccine antigen amount is from 1 to 5 mg/ml chimeric polypeptide. Vaccines can be administered by known techniques. In one embodiment the vaccine is administered via subcutaneous injection. In another embodiment the vaccine is administered by intradermal injection, intramuscular injection or infusion.

Vaccine embodiments of the invention can further include dispersing or wetting agents, suspension agents, or other like materials. For example, embodiments can include sterile oils, synthetic mono- or diglycerides, fatty acids or oleic acids.

Vaccines are typically prepared as sterile, aqueous solutions. These solutions are stable under conditions of manufacture and storage. In some aspects, additional agents can be included in the vaccine to prevent microorganism action, for example, antibacterial or antifungal agents.

Vaccine solutions of the invention are prepared by incorporating the materials in the required amounts (antigen, adjuvant, other ingredients) and can be followed by terminal sterilization, e.g., via UV light or ozone treatment. Alternatively, vaccine solutions of the invention can be prepared using individually sterilized components prior to final assembly (in which case no terminal sterilization is required).

Treatment progress for patients receiving vaccine embodiments of the invention can be monitored and additional administrations provided. Increase in growth hormone levels, increase in insulin-like growth factor 1 levels, and functional benefits (for example, acceptable weight loss in an obese patient) are all targets for monitoring of treatment effectiveness. In addition, where type 1 or 2 diabetes or obesity is being treated, blood glucose, IGF-1 levels, lipid profiles, insulin levels, and Hemoglobin Bound A1c (HbA1c) levels can be monitored to determine effectiveness of treatment on a patient. Based on an individual patients' progress, additional vaccine injections can be performed using more or less antigen in accordance with the present invention. In addition, alternative adjuvant combinations may be used to modify a particular patients' response to vaccination, as determined by the health care professional.

Embodiments herein can be combined with other conventional therapies for the target growth hormone and/or insulin-like growth factor 1 deficiency disease state or condition. For example, vaccinations of the invention can be combined with replacement insulin in the treatment of type 1 diabetes, or vaccinations can be combined with weight loss surgery or low calorie diets in a patient suffering from severe obesity.

Having generally described the invention, the same will be more readily understood by reference to the following examples, which are provided by way of illustration and are not intended as limiting.

EXAMPLES

The following examples are provided for illustrative purposes only and are not intended to limit the scope of the invention.

Example 1

Construction of CAT-Defective Somatostatin Fusion Protein

The present example illustrates the production of a CAT-defective somatostatin fusion protein in accordance with embodiments of the present invention. Site-directed mutagenesis was performed on plasmid pET30b-Cat-Som to replace His192 and His193 with glycine residues (after modification: Gly192 and Gly193). Inactivation of the His193 (and His192) residues eliminates the capacity of the CAT enzyme to accept protons, thereby providing complete inactivation of the CAT.

The spacer in the same pET30b-Cat-Som (having the His replacement(s)) was codon-optimized for expression by *E. coli* in the absence of co-expressed tRNA molecules.

The modified CAT-defective somatostatin nucleic acid construct is shown as SEQ ID NO: 12. The CAT-defective somatostatin fusion protein sequence is disclosed as SEQ ID NO: 13, being compared to an unmodified CAT-somatostatin fusion protein (SEQ ID NO: 14).

Example 2

CAT-Defective Somatostatin Fusion Protein can be Expressed at High Levels

The codon-optimized CAT-defective somatostatin construct as described in Example 1 was used to express the fusion protein in BL21(DE3) cells. Transformed cells were grown in LB and induced with 0.4 mM IPTG for approximately three hours. One milliliter of cells from a density of OD 0.7 culture were pelleted, and heated at 70° C. for ten minutes in 100 μl SDS sample buffer. A sample of 40 μl of cell extract was loaded per lane for SDS PAGE.

Figure 2:
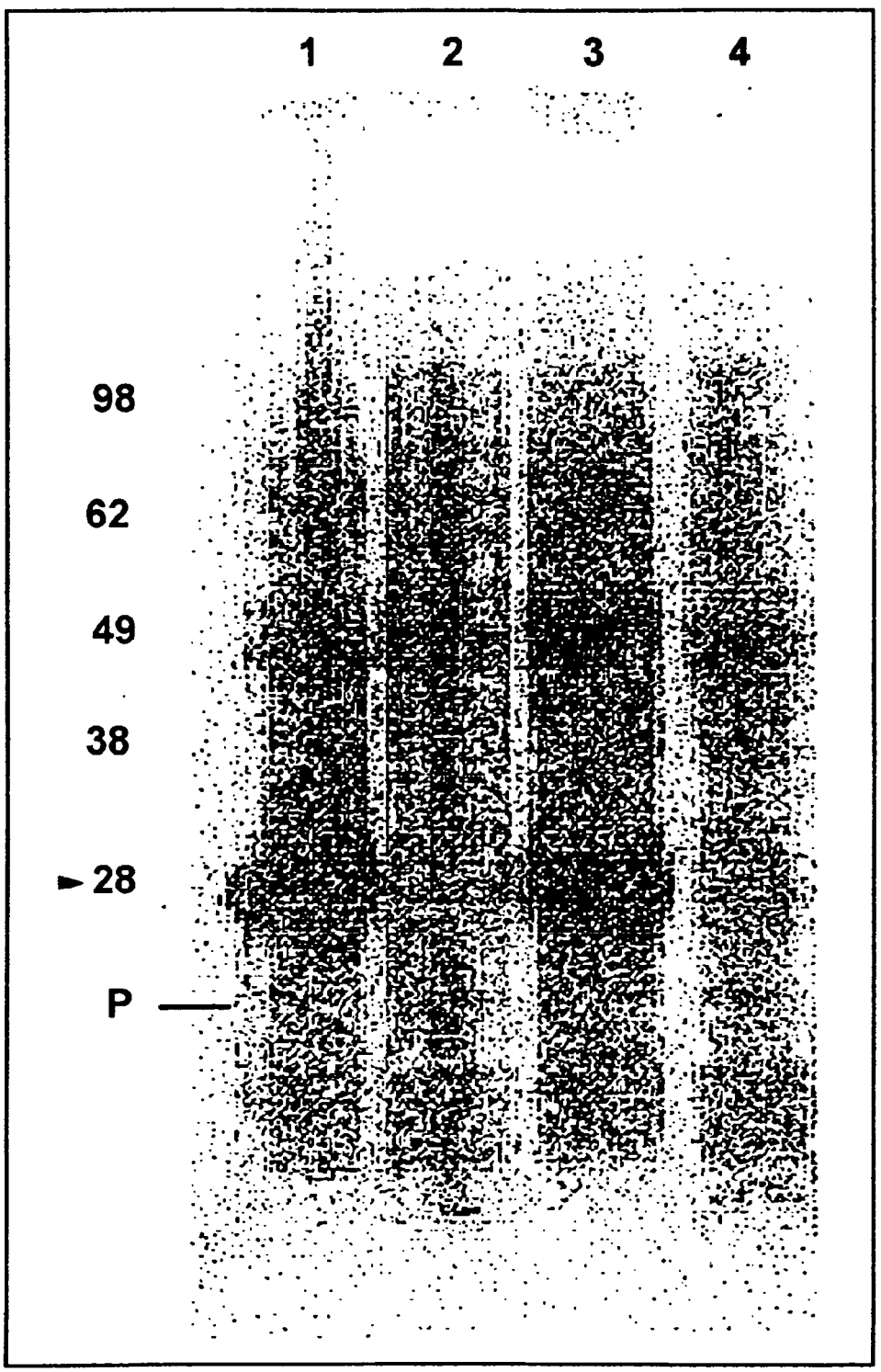
FIG. 2 is an illustrative stained SDS-PAGE showing a 28KD band corresponding to the predicted size of a codon-optimized, CAT-defective somatostatin polypeptide of the invention. Lane 1 is LB+IPTG, reduced, Lane 2 is LB, reduced, Lane 3 is LB+IPTG and Lane 4 is LB.

As shown in FIG. 2, a 28 KD band corresponding to the predicted size of a codon-optimized, CAT-defective somatostatin fusion protein was visible in lanes 1 (LB+IPTG, reduced) and 3 (LB+IPTG) after induction with IPTG. No expression is seen in control lanes 2 (LB, reduced) and 4 (LB). As expected, there was no difference in fusion protein size when run under standard or reducing conditions.

Example 3

Endotoxin Free, Codon-Optimized CAT-Deficient Somatostatin Containing Vaccine An illustrative vaccine in accordance with the present invention:

Reagent Solution:
1. Carbopol Base
   a. Dissolve 0.5 grams of Carbopol 974P in water or saline
   b. Mix and boil to dissolve. Followed by autoclaving.
   c. Store at 4° C.
2. Squalene Base
   a. Mix 58.1 ml of squalene, 4.6 ml of non-animal origin Tween 80 and 5.2 ml of Span 85.
   b. Mixture was filtered through a 0.2μ, filter.
   c. Store at 4° C.
3. Tragacanthin solution
   a. Extract tragacanth gum with methanol.
   b. Collect methanol insoluble fraction.
   c. Dry at room temperature.
   d. Store at room temperature in a desiccated state,
   e. Add 1 gram of dried Tragacanthin in water or saline.
   f. Mix and boil to dissolve, followed by autoclaving.
   g. Store at 4° C.

Vaccine Preparation
1. Vaccine antigens are prepared in saline or PBS at 5 mg/ml or lower.
2. Add 6.79 ml of squalene base to mixing bottle.
3. Add 10 ml of Carbopol base to Squalene base. (CS)
4. Mix well.
5. Add 10 ml of Tragacanthin solution to CS solution.
6. Mix well.
7. Vaccine antigens, undiluted or diluted to use in saline or PBS, are added to a final volume of 82 ml.
8. 1 ml of a 1% Thimerosal solution is added and mixed well.
9. Store vaccine at 4° C. until use.

Alternative illustrative vaccine in accordance with the present invention:

Reagent Solutions:
1. Carbopol Base:
   a. Dissolve 0.5 grams of Carbopol 974P in water or saline;
   a. Mix and boil to dissolve; and autoclave
   b. Store at 4° C.
2. Squalene Base:
   a. Mix 58.1 ml of squalene, 4.6 ml of non-animal origin Tween 80 and 5.2 ml of Span 85; and filter through 0.2μ, filter
   b. Store at 4° C.
3. Arabinogalactan solution:
   a. Add 1-10 grams of arabinogalactan into PBS or saline;
   b. Mix and boil to dissolve; and autoclave
   c. Store at 4° C.

Vaccine Preparation:
1. Vaccine antigens are prepared in saline or PBS at 5 mg/ml or lower;
2. Add 6.79 ml of squalene base to mixing bottle;
3. Add 10 ml of Carbopol base to the Squalene base;
4. Mix thoroughly and add 10 ml of arabinogalactan solution;
5. Antigens of the invention, undiluted or diluted, to use in saline or PBS, are added to a final volume of 82 ml.
6. 1 ml of a 1% thimerosal solution is added and the vaccine mixed; and
7. The vaccine stored at 4° C. until use.

Example 4

Treatment of Cardio Vascular Disease Using Vaccine of Example 3

The present Example uses rats with left ventricle dysfunction as prepared in the protocol published in Genentech, 1995. Two groups of rats are segregated (each member of each group having a ligated left coronary artery), a first treatment group receives the vaccinations of the invention and a second control group (no vaccination, but otherwise treated the same). Each member of the treatment group receives a vaccination and then 21 days later a second vaccination, administered intramuscularly (1 ml/dose). Serum IGF-1 levels and anti-somatostatin antibodies are measured at day 0, day 21 and day 42. At day 42, hemodynamic parameters are also measured in both groups as well as a determination of infarct size and cardiac index.

It is anticipated that the rat group receiving the two vaccinations, as described in Example 3, would have substantially improved cardiac function (decrease infarct size and improved cardiac index) as compared to the control group.

Example 5

Treatment of Obesity Using Vaccine of Example 3

A rat obesity model as described in Vickers et al (2001) will be used to determine the effect that vaccines of the invention have on obesity. Rats are fed a hypercaloric diet for 30 to 60 days. Hypercaloric rats will be weighed and separated into three groups—a saline control group and a vaccination group continued on a hypercaloric diet, and a normal caloric diet group. Rats receiving the vaccination will receive 2×1 ml dose intramuscularly at day zero and at day 21. All rats will be weighed weekly throughout the study period. At day 42, all rats will be weighed and serum collected for IGF-1 analysis, urea analysis and anti-somatostatin antibody levels.

It is expected that rats receiving the vaccinations as described in Example 3 will have substantially improved weight control over saline control groups and show corresponding serum results that correlate that weight control is due to growth hormone modification. The vaccinated group will show substantially the same weight control as the normal caloric intake group.

Example 6

Treatment of Growth Deficiency Using Vaccine of Example 3

Three week old Cox (CD) rats will be vaccinated monthly for 3 months using a 1 ml dose. Each vaccination will occur intramuscularly or subcutaneously. Control rats will receive saline injections, using the same mode of administration and the same volume of material for administration. All rats will be weighed to determine growth on a weekly basis and bled at 0, 4, 8, 12 and 16 weeks. Serum will be collected at a similar schedule and analyzed for IGF-1, urea and anti-somatostatin antibody levels.

It is expected that CD rats receiving vaccinations as described in Example 3 will have substantially improved growth as compared to control CD rats. Treated rats should show serum results that confirm vaccinations effects on treated rats.

Example 7

Increased Somatostatin Leads to Weight Gain in Mice

Mouse obesity studies were performed to see if exogenously administered somatostatin would cause weight gain in mice. A seven day study was performed on outbred mice where three different inventive adjuvants were combined with recombinant somatostatin (adjuvants are referred to as JH14, JH17 and JH18). Each adjuvant was spiked with 1 mg/ml recombinately produced somatostatin (produced in 2009) and one adjuvant (JH14) was also spiked with 2007 produced somatostatin at a concentration of 2.57 mg/ml. A control group of mice received a sterile saline injection.

Each mouse was weighed at the start of the study to determine a baseline weight. Vaccinations on each mouse were performed on day 0 by IP injection of 0.5 ml of vaccine. Somatostatin in JH17 and 18 adjuvants were administered to female mice and JH14 to male mice. Mice were fed a normal diet over the course of the 7 days with each mouse being re-weighed at day 7.

Figure 3:
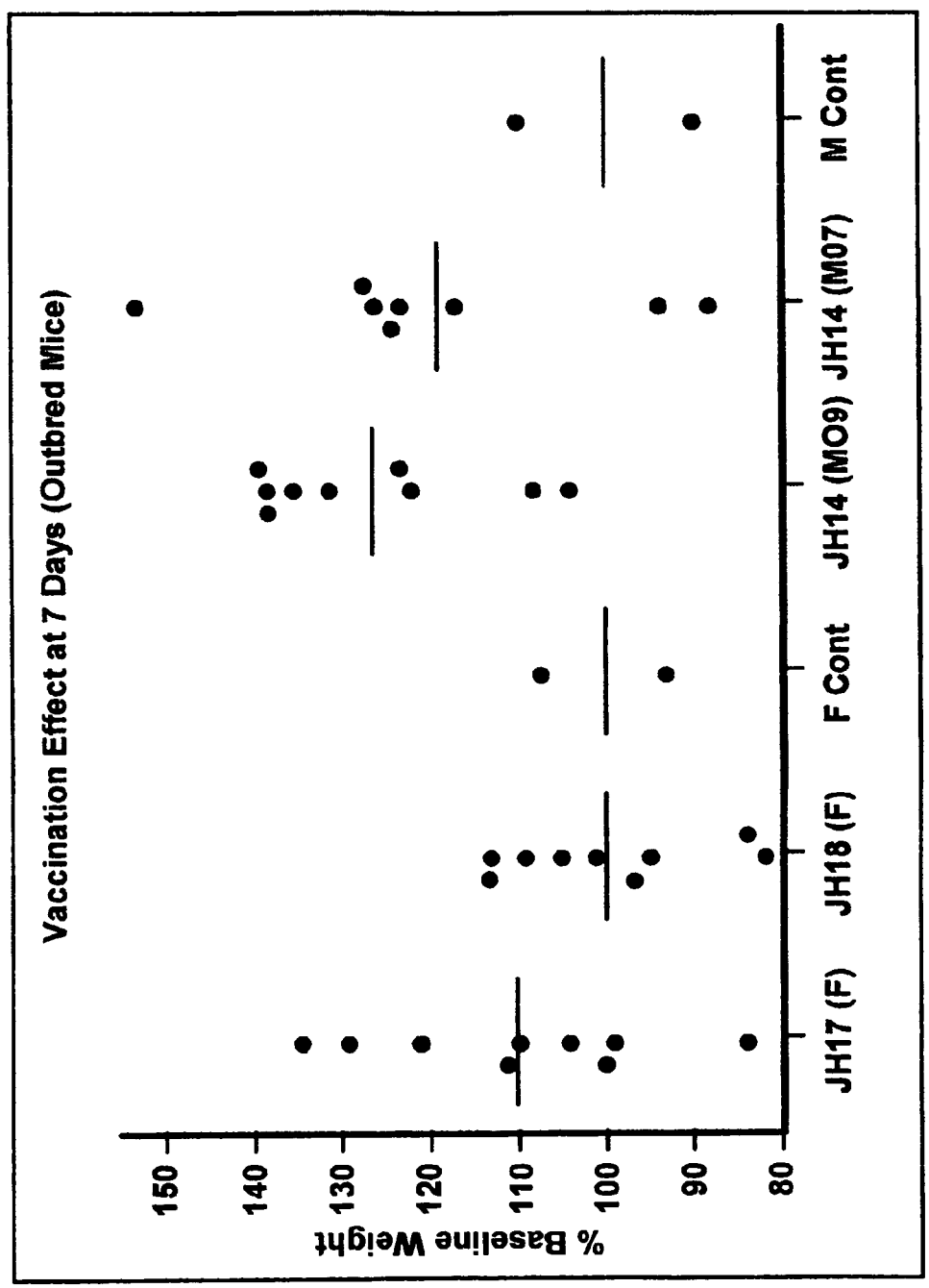
FIG. 3 is a scatter graph of percent baseline weight versus somatostatin containing vaccinations on outbred mice.

As shown in FIG. 3, outbred mice receiving somatostatin remained healthy and showed little adverse effects from the one week study. Female mice in the JH17 group had an increase in weight, while the female JH18 mice were similar in weight gain to control mice. Male mice in the two JH14 groups (2007 and 2009) both showed weight gain over control group male mice. Overall the findings in FIG. 3 illustrate that the JH14, JH17 and JH18 adjuvants are safe for use in mice, highly consistent and capable of storage, and that exogenously administered somatostatin generally results in weight increase in a target mouse, providing evidence that somatostatin is involved in weight gain. All of the effects occurred within several days of IP immunization. This is due to direct macrophage processing and antigen and presentation B lymphocytes at an accelerated rate, due to route of administration, the nature of the chimeric polypeptides and the adjuvant effect.

The JH14, 17 and 18 Preblends are as described in this and US Application S/N PCT/US08/68195, entitled Chloramphenicol Acetyl Transferase (CAT)-Defective Somatostatin Fusion Protein and Uses Thereof. The final formulation had 1 mg protein antigen per 1 ml dose. For this work the following were the formulations:

| JH17 | |
|---|---|
| Refolded protein | 12 ml (5.86 mg/ml) |
| Dulbecco's PBS | 24.5 ml |
| JH 17 Preblend | 13.4 ml |
| 1% Thimerosal | 0.5 ml |
| 37% formaldehyde | 0.1 ml |
| JH18 | |
| Refolded protein | 12 ml (5.86 mg/ml) |
| Dulbecco's PBS | 24.5 ml |
| JH 18 Preblend | 13.4 ml |
| 1% Thimerosal | 0.5 ml |
| 37% formaldehyde | 0.1 ml |
| JH14 | |
| Refolded protein | 12 ml (5.86 mg/ml) |
| Dulbecco's PBS | 27.8 ml |
| JH 14 Preblend | 10 ml |
| 1% Thimerosal | 0.5 ml |
| 37% formaldehyde | 0.1 ml |

Note that formulations above include thimerosal and formaldehyde to limit contamination of the vaccines. These materials are only used where multi-dose re-entry bottles for dispensing vaccine are in use, typically human and animal treatment protocols will be packaged in single-use vials, thereby eliminating the need for these preservatives. Also note that a higher level of antigen was used in the 2007 JH14 lot to make up for protein degradation.

Example 8

Treatment of Obesity in Mice

Mouse obesity studies were performed using mice from Jackson Laboratories, Bar Harbor, Me. A number of inbred mice from line C57BL/6J were obtained from Jackson Laboratories, the mice were: male, showed induced severe obesity, had polygenic genetics, and exhibited mature onset obesity. In previous testing, Jackson Laboratories had determined that this particular strain of mice, when fed on a high fat diet, develops metabolic syndrome phenotypes very similar in nature to those reported in the human population. For example, C57BL/6J mice fed a high fat diet will show visceral adiposity, insulin resistance, hyperinsulinemia, hyperleptinemia, leptin resistance and hypertension.

Studies were conducted to test the effectiveness of vaccine embodiments herein for treating obesity, i.e., including limiting weight gain in some mice to causing weight loss in C57BL/6J mice. Six week old mice were fed a 60% kcal % fat diet for 6 weeks. Twelve week old mice were then broken into one of four groups: group 1 included mice treated with JH14 containing vaccine; group 2 included mice treated with JH17 containing vaccine, group 3 included mice treated with JH18 containing vaccine, and group 4 included control mice that were treated with PBS rather than any type of anti-somatostatin type antigen. Mice in each group were vaccinated using a 0.5 ml of the specified vaccine or PBS via an IP route. After twenty two days the mice were treated again with a second IP dose using 0.1 ml of vaccine.

Figure 4:
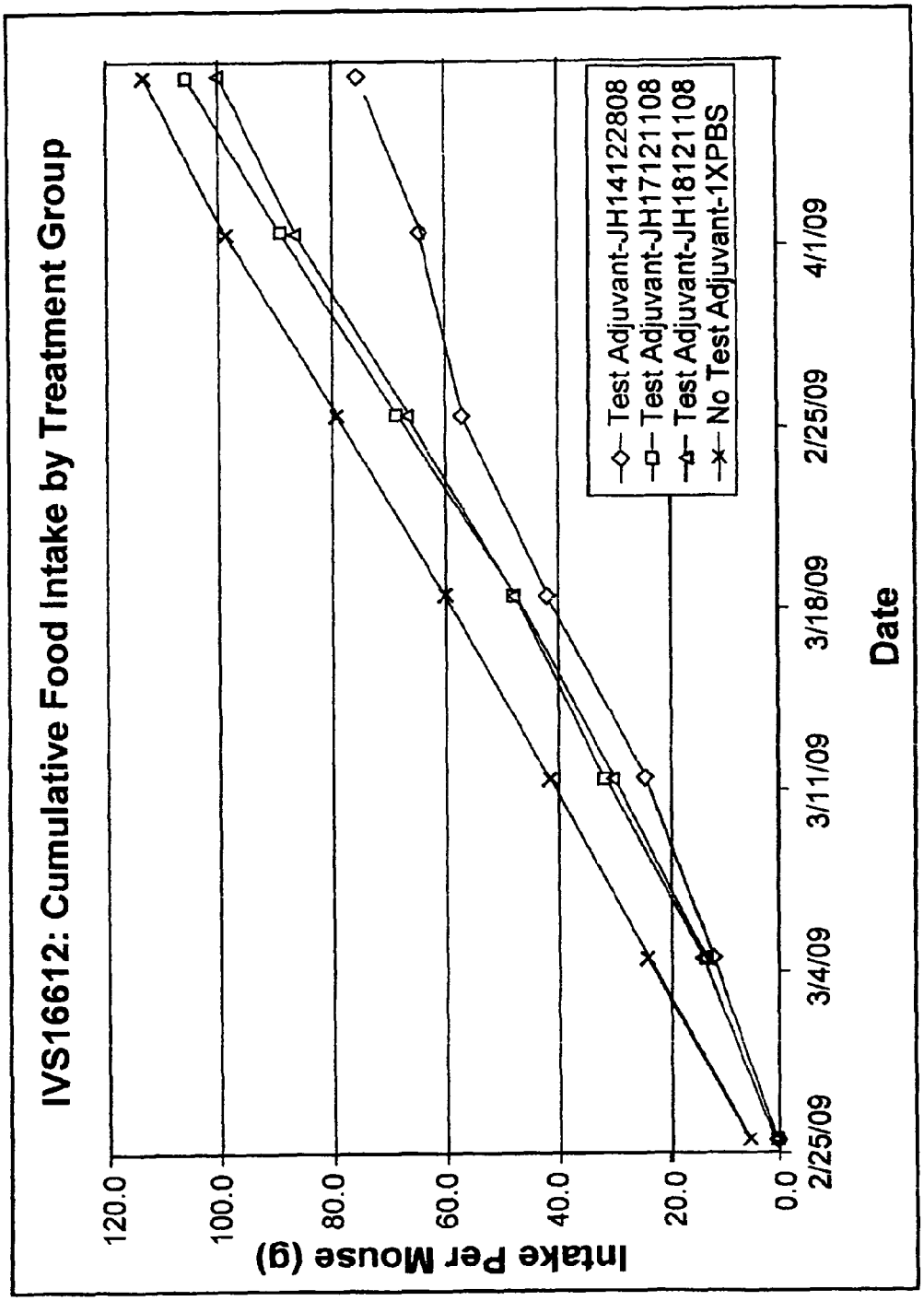
FIG. 4 is a graph showing the intake of food per group of mice over a course of 7 days.

Throughout the course of the study (6 weeks) each mouse was weighed two times per week and food intake monitored, i.e., to ensure that weight changes were not due to loss or increase in food intake (see FIG. 4 showing cumulative food intake within each of the 4 groups). A terminal bleed was performed on each mouse at the conclusion of the study and IGF-1 levels determined (IGF-1 plasma levels were determined using Diagnostic Systems Laboratories Inc. Active Mouse/Rat IGF-1 ELISA (DSL-10-29200).

Figure 5:
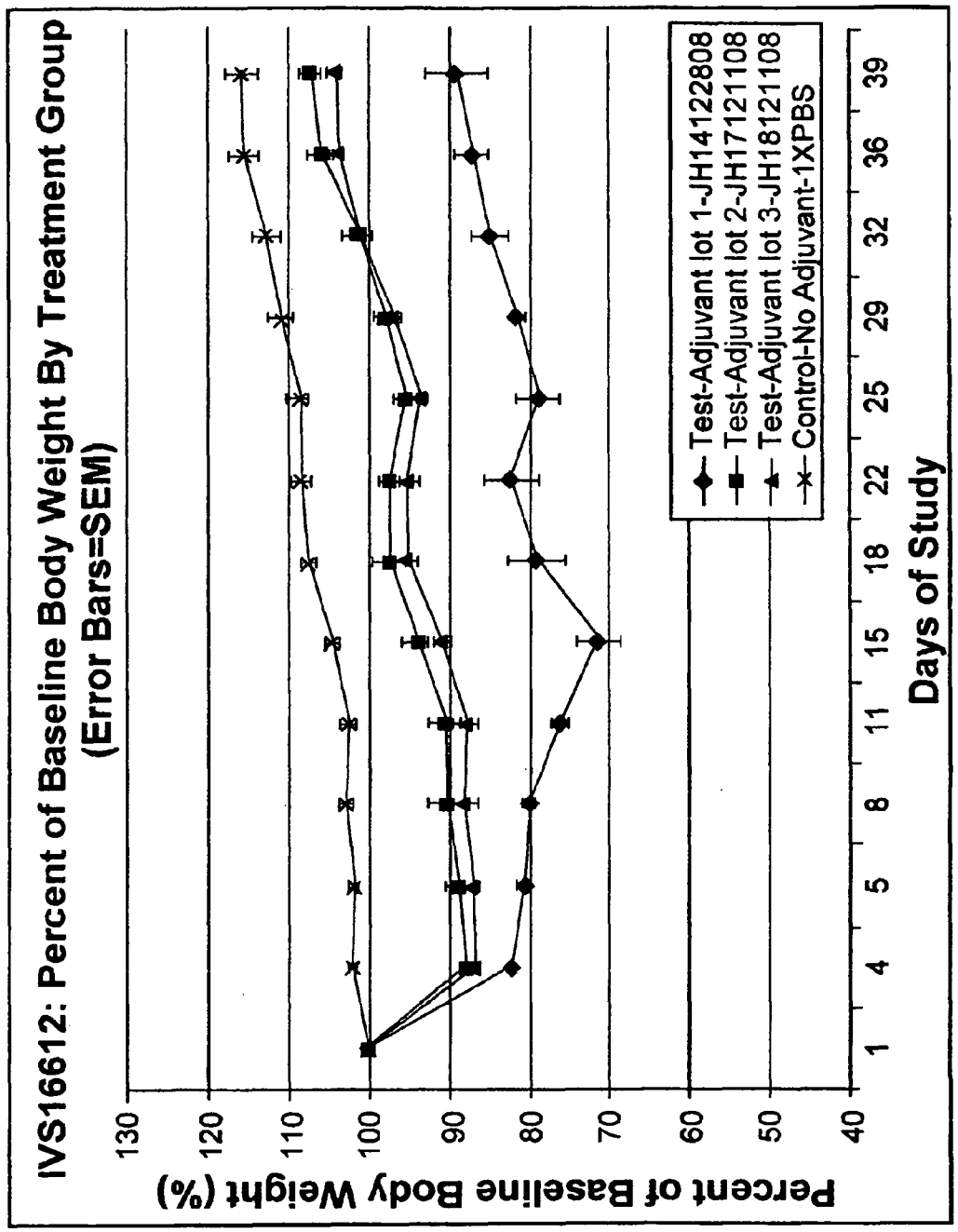
FIG. 5 is a graph showing the mean body weight of treatment groups of mice over the course of 39 days, each group tested is shown with an error bar.
Figure 6:
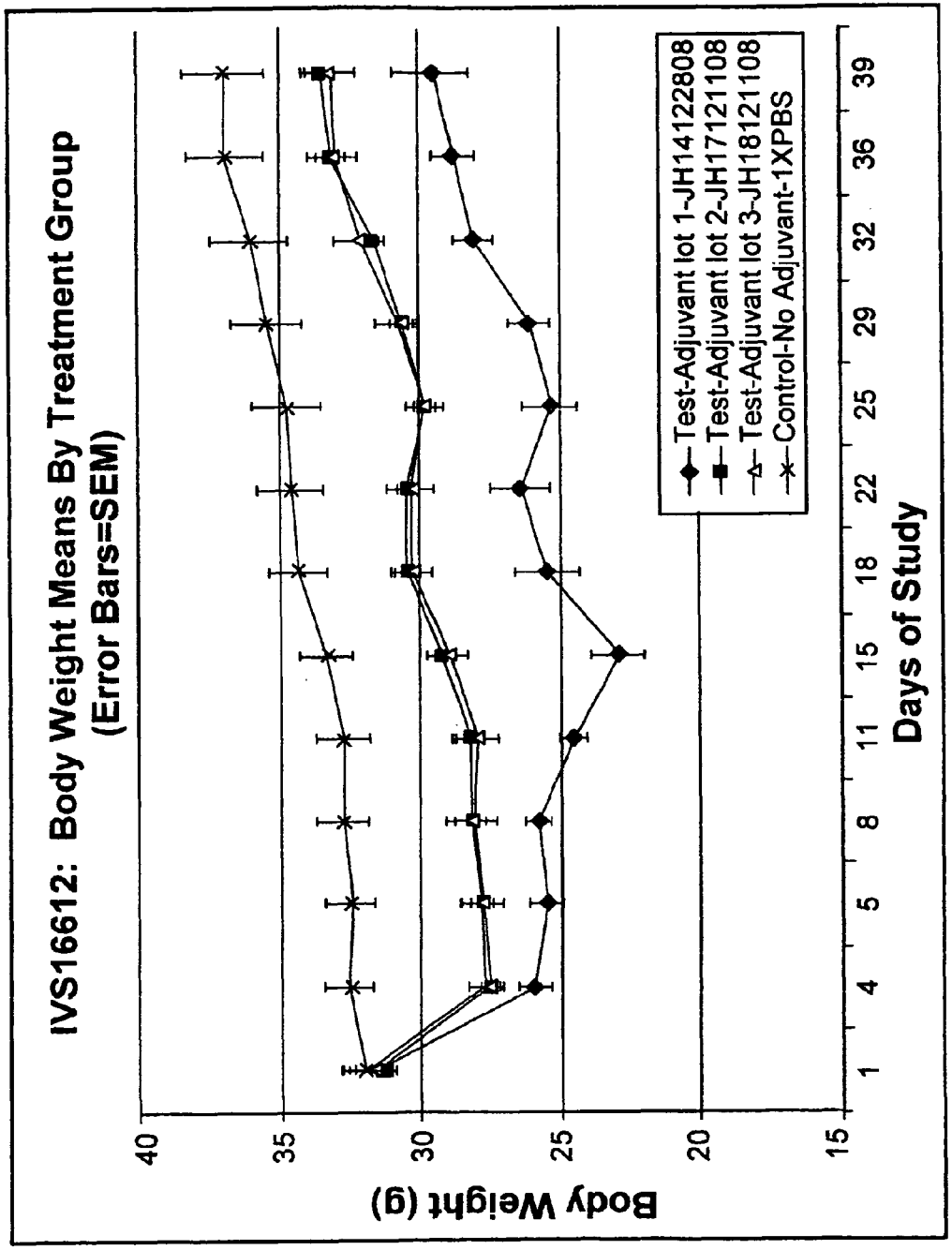
FIG. 6 is a graph showing percent of baseline body weight of treatment groups of mice over the course of 39 days, each group testing is shown with an error bar.

As shown in FIGS. 5 and 6 and Table 1, mice treated with JH14, 17 and 18 all showed a highly significant difference (p<0.0001) by parametric or non-parametric statistical analyses) in percent Final Body Weight vs. Baseline Weight. Significant weight loss was observed in each vaccinated group within the first 7 days while the control group showed sleight weight gain over the same time period. A small weight loss was also observed after the second dose of vaccine (⅕$^{th}$ dose provided on day 1) was administered to the JH14, JH17 and JH18 groups at day 22.

Data from the mouse obesity study provided the following conclusions: (1) although there is not a statistically significant difference between JH18 and the controls, in terms of IGF-1 ng/ml, there is a highly significant difference between these groups (P<0.0001) by parametric or non-parametric statistical analysis in percent Final Body Weight versus Baseline Weight; (2) In percent Final Body Weight versus Baseline Weight, JH17 versus the controls produced a statistically significant difference by both statistical tests; (3) JH18 (which had a mean IGF-1 level of 135.8 ng/ml more than JH17), demonstrated a statistically significant difference versus JH17 in percent baseline weight (only by the non-parametric test); (4) chimeric-somatostatin antigen of the invention in both JH17 and JH18 adjuvants induced a statistically significant difference in percent Final Body Weight versus Baseline Weight; (5) JH18 was statistically significant when compared with JH17 by non-parametric analysis in terms of percent Final Body Weigh versus Baseline Weight; (6) IGF-1 levels can be correlated with a greater weight loss at the end of the study versus both controls and JH17 vaccinates (see Table 2); (7) since all vaccinates had the same dose amounts of the chimeric-somatostatin antigen of the invention, an adjuvant affect was observed within the study; (8) inbred C57BL/6J male mice fed 60% kcal fat diet demonstrated a significant weight loss within the first week post IP vaccination; and (9) the weight loss shown herein persisted even while the mice ate a 60 kcal % fat diet for the duration of the study.

TABLE 1

Final Body Weight versus Baseline Weight

| Group | # | % Baseline | Standard Deviation | Mann Whitney (two tailed) | Unpaired t-test (two-tailed) |
|---|---|---|---|---|---|
| Controls | 10 | 115.5 | 6.3 | Not Done | Not Done |
| JH17 | 10 | 107.1 | 4.7 | P = 0.0021 | P = 0033 |
| JH18 | 10 | 104 | 3.0 | P < 0.0001 | P < 0.0001 |
| JH17 vs. JH18 | — | — | — | P = 0.0355 | P = 0.1016 |

TABLE 2

IGF-1 Statistical Analysis

| Group | # | Mean IGF-1 (ng/ml) | Standard Deviation | Mann Whitney (1 tailed) |
|---|---|---|---|---|
| Controls | 10 | 365.6 | 88.7 | Not Done |
| JH17 | 10 | 304.2 | 99.2 | P = 0.0827 |
| JH18 | 10 | 440.4 | 103.7 | P = 0.105 |

It is understood for purposes of this disclosure, that various changes and modifications may be made to the invention that are will within the scope of the invention. Numerous other changes may be made which will readily suggest themselves to those skilled in the art and which are encompassed in the spirit of the invention disclosed herein and as defined in the appended claims. The specification contains numerous citations to patents and publications. Each is hereby incorporated by reference for all purposes.

What is claimed is:

1. A method for treatment of obesity in a patient comprising: administering an immunogenic amount of a vaccine to the obese patient wherein the vaccine comprises (a) a chimeric polypeptide of somatostatin-14 attached to an inactivated chloramphenicol acetyl transferase (CAT) enzyme and (b) an adjuvant.

2. The method of claim 1 wherein the patient is a human, dog, cat or horse.

* * * * *